(12) United States Patent
Stanton et al.

(10) Patent No.: US 6,939,847 B2
(45) Date of Patent: Sep. 6, 2005

(54) USE OF COLOSTRININ, CONSTITUENT PEPTIDES THEREOF, AND ANALOGS THEREOF, AS OXIDATIVE STRESS REGULATORS

(75) Inventors: G. John Stanton, Texas City, TX (US); Thomas K. Hughes, Jr., Galveston, TX (US); Istvan Boldogh, Galveston, TX (US)

(73) Assignee: Board of Regents, The University of Texas System, Austin, TX (US)

(*) Notice: Subject to any disclaimer, the term of this patent is extended or adjusted under 35 U.S.C. 154(b) by 83 days.

(21) Appl. No.: 10/281,652

(22) Filed: Oct. 28, 2002

(65) Prior Publication Data

US 2003/0091606 A1 May 15, 2003

Related U.S. Application Data

(62) Division of application No. 09/641,803, filed on Aug. 17, 2003, now Pat. No. 6,500,798.
(60) Provisional application No. 60/149,310, filed on Aug. 17, 1999.

(51) Int. Cl.$^7$ .................. A61K 38/00; A61K 38/08; A61K 35/20; C07K 14/47
(52) U.S. Cl. .................. 514/2; 514/12; 514/13; 514/14; 514/15; 514/16; 514/17; 514/18; 530/300; 530/350; 530/324; 530/326; 530/327; 530/328; 530/329; 530/334; 424/535
(58) Field of Search .................. 514/2, 12–18; 530/300, 350, 324, 326, 327, 328, 334, 329; 424/535

(56) References Cited

U.S. PATENT DOCUMENTS

| | | |
|---|---|---|
| 4,938,949 A | 7/1990 | Borch et al. |
| 5,595,887 A | 1/1997 | Coolidge et al. |
| 6,040,180 A | 3/2000 | Johe |
| 6,410,058 B2 | 6/2002 | Gohlke et al. |
| 6,500,798 B1 | 12/2002 | Stanton et al. |

FOREIGN PATENT DOCUMENTS

| | | |
|---|---|---|
| JP | 06 041191 A | 2/1994 |
| WO | WO 95/00155 | * 1/1995 |
| WO | WO 95/30686 | 11/1995 |
| WO | WO 98/14473 | 4/1998 |
| WO | WO 99/65329 | 12/1999 |
| WO | WO 00/75173 | 12/2000 |
| WO | WO 01/11937 | 2/2001 |
| WO | WO 01/12650 | 2/2001 |
| WO | WO 01/12651 | 2/2001 |
| WO | WO 02/13849 | 2/2002 |
| WO | WO 02/13850 | 2/2002 |
| WO | WO 02/13851 | 2/2002 |
| WO | WO 04/37851 | 5/2004 |

OTHER PUBLICATIONS

Babbit, ed., *The Vanderbilt Rubber Handbook*, R.T. Vanderbilt Company, Inc., Norwalk, CT, pp. 344–397 (1978).
Bespalov et al., "Fabs specific for 8–oxoguanine: control of DNA binding," *J Mol Biol.* Nov. 12, 1999;293(5):1085–95.
Blach–Olszewska et al., "Stimulatory effect of ovine colostrinine (a proline–rich polypeptide) on interferons and tumor necrosis factor production by murine resident peritoneal cells,"*Arch Immunol Ther Exp (Warsz)*. 1997;45(1):43–7.
"Blast," National Institutes of Health [online] Bethesda, M.D. Retrieved from the Internet on May 14, 2001:<URL:http://www.ncbi.nlm.nih.gov/gorf/b12.html>, 1 pg.
Jurgens et al., "Modification of Human Low–Density Lipoprotein by the Lipid Peroxidation Product 4–Hydroxynonenal," *Biochem Biophys.,* Jan. 1986;875:103–114.
Boldogh et al., "Modulation of 4HNE–Mediated Signaling by proline–rich peptides from Ovine Colostrum," *J Mol Neuroscience,* May 2003;20(2): 125–134.
Brown et al., "7–Hydroperoxycholesterol and its products in oxidized low density lipoprotein and human atherosclerotic plaque," *J. Lipid Res,* 1997;38: 1730–1745.
Bruce–Keller et al., "4–Hydroxynonenal, a product of lipid peroxidation, damages cholinergic neurons and impairs visuospatial memory in rats," *J Neuropathol Exp Neurol,* 1998;57: 257–267.
Buettner, G.R., "The pecking order of free radicals and antioxidants: lipid peroxidation, alpha–tocopherol, and ascorbate," *Arch Biochem Biophys,* 1993;300: 535–543.
Cadenas et al., "Mitochondrial free radical generation, oxidative stress, and aging," *Free Radic Biol Med,* 2000;29:222–230.
Camandola et al., "The lipid peroxidation product 4–hydroxy–2,3–nonenal inhibits constitutive and inducible activity of nuclear factor kappa B in neurons," *Brain Res Mol Brain Res,* 2000;85:53–60.
Cheng et al., "Effects on mGST A4 transfection on 4–hydroxynonenal–mediated apoptosis and differentiation of K562 human erythroleukemia cells," *Arch Biochem Biophys,* 1999;372: 29–36.
Davies et al., "Photo–oxidation of proteins and its role in cataractogenesis," *J. Photochem. Photobiol B,* 2001;63: 114–125.
Davis et al., "Cellular thiols and reactive oxygen species in drug–induced apoptosis," *J. Pharmacol Exp Ther,* 2001;296: 1–6.
DeZwart et al., "Biomarkers of free radical damage applications in experimental animals and in humans," *Free Radic Biol Med,* 1999; 26:202–226.

(Continued)

Primary Examiner—Jon Weber
Assistant Examiner—Chih-Min Kam
(74) *Attorney, Agent, or Firm*—Mueting, Raasch & Gebhardt, P.A.

(57) ABSTRACT

The present invention provides methods that utilize compositions containing colostrinin, an constituent peptide thereof, an active analog thereof, and combinations thereof, as an oxidative stress regulator.

24 Claims, 8 Drawing Sheets

OTHER PUBLICATIONS

Evan et al., "A matter of life and cell death," *Science,* 1998; 281: 1317–1322.

Finkel et al., "Oxidants, oxidative stress and the biology of ageing," *Science,* 1998;281: 1317–1322.

Friguet et al., "Protein degradation by the proteasome and its implications in aging," *Ann N Y Acad Sci,* 2000;908: 143–154.

Gage et al., "Isolation, Characterization, and use of Stem Cells from the CNS,"*Annu. Rev. Neurosci,* 1995;18: 159–92.

Gardner et al., "Development of a peptide antibody specific to human glutathione S–transferase alpha 4–4 (hGSTA4–4) reveals preferential localization in human liver mitochondria," *Arch Biochem Biophys,* 2001;390: 19–27.

Hainut et al., "Redox modulation of p53 conformation and sequence–specific DNA binding in vitro," *Cancer Res,* 1993;53: 4469–4473.

Han et al., "Implication of a small GTPase Rac1 in the activation of c–Jun–N–terminal kinase and heat shock factor in response to heat shock,", *J Biol Chem,* 2001; 276:1889–1895.

Hughes et al., "Mediation of nerve growth factor–driven cell cycle arrest in PC12 cells by p53. Simultaneous differentiation and proliferation subsequent to p53 functional inactivation," *J Biol Chem,* 2000;275: 37829–37837.

Keller et al., "Mitochondrial manganese superoxide dismutase prevents neural apoptosis and reduces ischemic brain injury: suppression of peroxynitrite production, lipid peroxidation, and mitochondrial dysfunction," *J Neurosci,* 1998;18: 687–697.

Kong et al., "Signal transduction events elicited by natural products: a role of MAPK and caspase pathways in homeostatic response and induction of apoptosis,"*Arch Pharm Res,* 2000;23: 1–16.

Kruman et al., "Evidence that 4–hydroxynonenal mediates oxidative stress–induced neuronal apoptosis," *J Neurosci,* 1997;17:5089–5100.

Lafon–Cazal et al., "Nitric oxide, superoxide and peroxynitrite: putative mediators of NMDA–induced cell death in cerebellar granule cells," *Neuropharmacology,* 1993;32: 1259–1266.

Leonarduzzi et al., "Lipid oxidation products in cell signaling," *Free Radic Biol Med,* 2000;28: 1370–1378.

Ley et al., "Adhesion Molecules in Lymphocyte Trafficking and Colitis," *Gastroenterology,* Oct. 2001;121(4);Editorial:1008–1010.

Mattson et al., "Alzheimer's disease. Short Precursor shortens memory," *Nature,* 1997;387: 457–458.

Nakamura et al., "Redox regulation of cellular activiation," *Annu Rev Immunol,* 1997;15: 351–369.

Page et al., "4–Hydroxynonenal prevents NF–kappaB activation and tumor necrosis factor expression by inhibiting IkappaB phosphorylation and sebsequent proteolysis," *J Biol Chem,* 1999;274:11611–11618.

Parola et al., "HNE interacts directly with JNK isoforms in human hepatic stellate cells," *J Clin Invest,* 1998;102:1942–1950.

Perkins et al., "Association of antioxidants with memory in a multiethnic elderly sample using the Third National Health and Nutrition Examination Survey,"*Am J Epidemiol,* 1999;150: 37–44.

Perrig et al., "The relation between antioxidants and memory performance in the old and very old," *J Am Geriatr Soc,* 1997;45: 718–724.

Poli et al., "4–Hydroxynonenal in the pathomechanisms of oxidative stress,"*IUBMB Life,* 2000;50: 315–321.

Rivas–Arancibia et al., "Effects of ozone exposure in rats on memory and levels of brain and pulmonary superoxide dismutase," *Environ Res,* 1998;76: 33–39.

Ross et al., "Atherosclerosis: a cancer of the blood vessels?," *Am J Clin Pathol 116 Suppl,* 2001:S97–107.

Rusnak et al., "Sensing electrons: protein phosphatase redox regulation," *Trends Biochm Sci,* 2000;25: 527–529.

Salmi et al., "Immune Cell Trafficking in Uterus and Early Life is Dominated by the Mucosal Addressin MadCAM–1 in Humans," *Gastroenterology,* Oct. 2001;121(4): 853–864.

Sano et al., "A controlled trial of selegiline, alpha–tocopherol, or both as treatment for Alzheimer's disease," *The Alzheimer's Disease Cooperative Study, N Engl J Med,* 1997;336:1216–1222.

Sayre et al., "4–Hydroxynonenal–derived advanced lipid peroxidation end products are increased in Alzheimer's disease," *J Neurochem,* 1997;68: 2092–2097.

Senft et al., "Determining glutathione and glutathione disulfide using the fluroescense probe o–phthaladehyde," *Anal Biochem,* 2000; 280: 80–86.

Sinclair et al., "Altered plasma antioxidant status in subjects with Alzheimer's disease and vacular dementia," *Int J Geriatr Psychiatry,* 1998;13: 840–845.

Uchida et al., "Modification of histidine residues in proteins by reaction with 4–hydroxynonenal," *Proc Natl Acad Sci USA,* 1992;89:4544–4548.

Vaglini et al., "Cytochrome P450 and parkinsonism: protective role of CYP2E1," *Funct Neurol,* 2001;16: 107–112.

Woods et al., "Regulation of p53 function," *Exp Cell Res,* 2001;264: 56–66.

Yoritaka et al., "Immunohistochemical detection of 4–hydroxynonenal protein adducts in Parkinson disease," *Proc Natl Acad Sci USA,* 1996:93: 2696–2701.

Zimecki et al., "Immunotropic properties of fractions isolated from human milk," *Arch Immunol Ther Exp,* 1984;32: 203–209.

Zimecki et al., "The effect of a proline–rich polypeptide (PRP) on the humoral immune response. II. PRP induces differentiation of helper cells from glass–nonadherent thymocytes (NAT) and suppressor cells from glass–adherent thymocytes (GAT)," *Arch Immunol Ther Exp,* 1984;32: 197–201.

Zimecki et al., "The effect of a poline–rich polypeptide (PRP) on the humoral immune response. I. Distinct effect of PRP on the T cell properties of mouse glass–nonadherent (NAT) and glass–)adherent (GAT) thymocytes in thymectomized mice," *Arch Immunol Ther Exp,* 1984;32: 191–196.

Janusz et al., "Immunoregulatory properties of synthetic peptides, fragments of a proline–rich polypeptide (PRP) from ovine colostrum," *Molecular Immunology,* Oct. 1987;24(10): 1029–1031.

"Ulta.com the Ultimate Beauty Site: Ingredients Q &A", [online].[retrieved on Aug. 20, 2004]. Retrieved from the Internet:www.ulta.com/control/qa_ingredients/; 8 pgs.

Altin et al., "Differential Induction of Primary–response (TIS) Genes in PC12 Pheochromocytoma Cells and the Unresponsive Variant PC12nnr5," *Journal of Biological Chemistry,* Mar. 25, 1991;266(9): 5401–5406.

Anneren et al., "GTK, a Src–related Tyrosine Kinase, Induces Nerve Growth Factor–independent Neurite Outgrowth in PC 12 Cells through Activation of the Rap 1 Pathway," *Journal of Biological Chemistry*, Sep. 15, 2000;275(37): 29153–29161.

Bagchi et al., "Comparative in vitro and in vivo protein kinase C activation by selected pesticides and transition metal salts," *Toxicology Letters*, 1997;91: 31–37.

Chen et al., "Lithium Increase Tyrosine Hydroxylase Levels both In Vivo and In Vitro," *Journal of Neurochemistry*, 1998;70(4): 1768–1771.

Cui et al., "Effects of Nucleoside Analogs on Neurite Regeneration and Mitochondrial DNA Synthesis in PC–12 Cells," *Journal of Pharmacology and Experimental Therapeutics*, 1997;280(3): 1228–1234.

Dagå et al., "NS 1231, a novel compound with neurotrophic–like effects in vitro and in vivo," *Journal of Neurochemistry*, 2002;81: 17–24.

DeJongh et al., "Estimation of Systemic Toxicity of Acrylamide by Integration of in vitro Toxicity Data with Kinetic Data with Kinetic Simulations," *Toxicology and Applied Pharmacology*, 1999;158: 261–268.

Doye et al., "Phosphorylation of Stathmin and Other Proteins Related to Nerve Growth Factor–induced Regulation of PC12 Cells," *Journal of Biological Chemistry*, Jul. 15, 1990;265(20): 11650–11655.

Feng et al., "NF–κB/Rel Proteins are Required for Neuronal Differentiation of SH-SY5Y Neuroblastoma Cells," *Journal of Biological Chemistry*, Oct. 22, 1999;274(43): 30341–30344.

Kim et al., "Insulin–like Growth Factor–I–mediated Neurite Outgrowth in Vitro Requires Mitogen–activated Protein Kinase Activation,"*Journal of Biological Chemistry*, Aug. 2, 1997;272(34): 21268–21273.

Kim et al., "Differential Regulation of Insulin Receptor Substrate–2 and Mitogen–Activated Protein Kinase Tyrosine Phosphorylation by Phosphatidylinositol 3–Kinase Inhibitors in SH-SY5Y Human Neuroblastoma Cells," *Endocrinology*, 1998;139(12): 4881–4889.

Lachyankar et al., "A Role for Nuclear PTEN in Neuronal Differentiation," *Journal of Neuroscience*, Feb. 15, 2000;20(4): 1404–1413.

Noble et al., "Overexpression of Dynamin is Induced by Chronic Stimulation of μ– but Not δ–Opioid Receptors: Relationships with μ–Related Morphine Dependence," *Molecular Pharmacology*, 2000;58: 159–166.

Ponthan et al., "The Synthetic Retinoid RO 13–6307 induces Neuroblastoma Differentiation in vitro and inhibits Neuroblastoma Tumour growth in vivo," *Int. J. Cancer*, 2003;104: 418–424.

Puglianiello et al., "IGF–I stimulates chemotasix of human neuroblasts. Involvement of type 1 IGF receptor, IGF binding proteins, phosphatidylinositol–3 kinase pathway and plasmin system," *Journal of Endocrinology*, 2000;165: 123–131.

Xiang–Ming et al., "Gating kinetics of potassium channel and effects of nerve growth factors in PC12 cells analyzed with fractal model," *Acta Pharmacol Sin*, Feb. 2001;22(2): 103–110.

Buescher et al., "Colostral antioxidants: separation and characterization of two activities in human colostrum," *J Pediatr Gastroenterol Nutr*1. Jan. 1992;14(1):47–56.

Calingasan et al., "Protein–bound acrolein: a novel marker of oxidative stress in Alzheimer's disease," *J Neurochem.* Feb. 1999;72(2):751–6.

Chao "Growth factor signaling: where is the specificity?" *Cell.* Mar. 20, 1992;68(6):995–7.

Elgert, "Immunology: Understanding the Immune System," Text (1996) Wiley–Liss $1^{st}$ Ed. pp. 24–26 and 199–217.

Esterbauer et al., "Chemistry and biochemistry of 4–hydroxynonenal, malonaldehyde and related aldehydes," *Free Radic Biol Med.* 1991;11(1):81–128.

Fields et al., *Synthetic Peptides: A User's Guide*, W.M. Freeman & Company, New York, NY, pp. 77–183 (1992).

Fillmore et al., "Differentiation of PC12 cells with nerve growth factor is associated with induction of transin synthesis and release," *J Neurosci Res.* Apr. 1992;31(4):662–9.

Gabbita et al., "Increased nuclear DNA oxidation in the brain in Alzheimer's disease," *J Neurochem.* Nov. 1998;71(5):2034–40.

Gabbita et al., "Decrease in peptide methionine sulfoxide reductase in Alzheimer's disease brain," *J Neurochem.* Oct. 1999;73(4):1660–6.

Good et al., "Evidence of neuronal oxidative damage in Alzheimer's disease," *Am J Pathol.* Jul. 1996;149(1):21–8.

Gratama et al., "Flow cytometric quantitation of immunofluorescence intensity: problems and perspectives. European Working Group on Clinical Cell Analysis,"*Cytometry.* Oct. 1, 1998;33(2):166–78.

Grunwald et al., "In situ analysis of chromatin proteins during development and cell differentiation using flow cytometry," *Methods Mol Biol.* 1999;119:443–54.

Hensley et al., "Brain regional correspondence between Alzheimer's disease histopathology and biomarkers of protein oxidation," *J Neurochem.* Nov. 1995;65(5):2146–56.

Hughes et al., "Modulation of immune responses by anabolic androgenic steroids," *Int J Immunopharmacol.* Nov. 1995;17(11):857–63.

Inglot et al., "Colostrinine: a proline–rich polypeptide from ovine colostrum is amodest cytokine inducer in human leukocytes," *Arch Immunol Ther Exp (Warsz).* 1996;44(4):215–24.

Inglot et al., "Colostrinin for treatment of Alzheimer's disease," *European Cytokine Network.* Sep. 1996;7(3):458(abstract 51).

Inglot et al., "Tumor–associated antigens are cytokine inducers and hypereactivity factors to the immune system," *Biotherapy.* 1998;11(1):27–37.

Janusz et al., "Isolation and characterization of a proline–rich polypeptide from ovine colostrum," *FEBS Lett.* Dec. 15, 1974;49(2):276–9.

Janusz et al., "Chemical and physical characterization of a proline–rich polypeptide from sheep colostrum," *Biochem J* Oct. 1, 1981;199(1):9–15.

Janusz et al., "Proline–rich polypeptide (PRP)—an immunomodulatory peptide from ovine colostrum," *Arch Immunol Ther Exp (Warsz).* 1993;41(5–6):275–9.

Kim et al., "Simultaneous differentiation and quantitation of erythroblasts and white blood cells on a high throughput clinical haematology analyser," *Clin Lab Haematol.* Feb. 1998;20(1):21–9.

Kooy et al., "Oxidation of 2',7'–dichlorofluorescin by peroxynitrite," *Free Radic Res.* Sep. 1997;27(3):245–54.

LeBel et al., "Evaluation of the probe 2',7'-dichlorofluorescin as an indicator of reactive oxygen species formation and oxidative stress," *Chem Res Toxicol.* Mar.–Apr. 1992;5(2):227–31.

Leszek et al., "Colostrinin: a proline-rich polypeptide (PRP) complex isolated from ovine colostrum for treatment of Alzheimer's disease. A double-blind, placebo-controlled study," *Arch Immunol Ther Exp (Warsz).* 1999;47(6):377–85.

Levi et al., "The mode of action of nerve growth factor in PC12 cells," *Mol Neurobiol.* Fall 1988;2(3):201–26.

Lovell et al., "Elevated thiobarbituric acid-reactive substances and antioxidant enzyme activity in the brain in Alzheimer's disease," *Neurology,* Aug. 1995;45(8):1594–601.

Lovell et al., "Elevated 4-hydroxynonenal in ventricular fluid in Alzheimer's disease," *Neurobiol Aging.* Sep.–Oct. 1997;18(5):457–61.

Lovell et al., "Decreased glutathione transferase activity in brain and ventricular fluid in Alzheimer's disease," *Neurology.* Dec. 1998;51(6):1562–6.

Lovell et al., "Increased DNA oxidation and decreased levels of repair products in Alzheimer's disease ventricular CSF," *J Neurochem.* Feb. 1999;72(2):771–6.

Lovell et al., "Decreased base excision repair and increased helicase activity in Alzheimer's disease brain," *Brain Res.* Feb. 7, 2000;855(1):116–23.

Markesberry, "Oxidative stress hypothesis in Alzheimer's disease," *Free Radic Biol Med.* 1997;2391):134–47.

Markesbery et al., "Four-hydroxynonenal, a product of lipid peroxidation, is increased in the brain in Alzheimer's disease," *Neurobiol Aging.* Jan.–Feb. 1998;19(1):33–6.

Markesbery et al. "Oxidative alterations in Alzheimer's disease," *Brain Pathol.* Jan. 1999;9(1):133–46.

Marshall et al., "Specificity of receptor tyrosine kinase signaling: transient versus sustained extracellular signal-regulated kinase activation," *Cell.* Jan. 27, 1995;80(2):179–85.

McHeyzer-Williams et al., "Enumeration and characterization of memory cells in the TH compartment," *Immunol. Rev.* Apr. 1996;150:5–21.

Mecocci et al., "Oxidative damage to mitochondrial DNA is increased in Alzheimer's disease," *Ann Neurol.* Nov. 1994;36(5):747–51.

Mishell et al., *Selected Methods in Cellular Immunology,* W.H. Freeman, San Francisco, CA; title page and table of contents only, 9 pages (1980).

Montine et al., "Cerebrospinal fluid F2-isoprostane levels are increased in Alzheimer's disease," *Ann Neurol.* Sep. 1998;44(3):410–3.

Ngo et al., "Computational Complexity, Protein Structure Prediction, and the Levinthal Paradox," (1994) *The Protein Folding Problem and Tertiary Structure Prediction* (#14), 491–495.

Ostrea et al., "Influence of breast-feeding on the restoration of the low werum concentration of vitamin E and beta-carotene in the newborn infant," *Am J Obstet Gynecol.* May 1986;154(5):1014–7.

Peunova et al., "Nitric oxide triggers a switch to growth arrest during differentiation of neuronal cells,"*Nature,* May 4, 1995;375(6526):68–73.

Piasecki et al., "Coincidence between spontaneous release of interferon and tumor necrosis factor by colostral leukocytes and the production of a colostrinine by human mammary gland after normal delivery," *Arch Immunol Ther Exp (Warsz).* 1997;45(1):109–17.

Popik et al., "Colostrinin, a polypeptide isolated from early milk, facilitates learning and memory in rats," *Pharmacol Biochem Behav.* Sep. 1999;64(1):183–9.

Prasad et al., "Regional membrane phospholipid alterations in Alzheimer's disease," *Neurochem Res.* Jan. 1998;23(1):81–8.

Rao, "Multipotent and Restricted Precursors in the Central Nervous System," (1999) *The Anatomical Record (New Anat.)* 257:137–148.

Roberts II et al., "Formation of isoprostane-like compounds (neuroprostanes) in vivo from docosahexaenoic acid,"*J Biol Chem.* May 29, 1998;273(22):13605–12.

Rothe et al., "Flow cytometric analysis of respiratory burst activity in phagocytes with hydroethidine and 2',7'-dichlorofluorescin," *J Leukoc Biol.* May 1990;47(5):440–8.

Royall et al., "Evaluation of 2',7'-dichlorofluorescin and dihydrorhodamine 123 as fluorescent probes for intracellular $H_2O_2$ in cultured entothelial cells," *Arch Biochem Biophys.* May 1993;302(2):348–55.

Schwab, "Repairing the Injured Spinal Cord," (2002) *Science* 295:1029–1031.

Shacter et al., "Differential susceptibility of plasma proteins to oxidative modification: examination by western blot immunoassay," *Free Radic Biol Med.* Nov. 1994;17(5):429–37.

Singh et al., "Dietary intake, plasma levels of antioxidant vitamins, and oxidative stress in relation to coronary artery disease in elderly subjects," *Am J Cardiol.* Dec. 15, 1995;76(17):1233–8.

Smith et al., "Advanced Maillard reaction end products are associated with Alzheimer disease pathology," *Proc Natl Acad Sci U S A.* Jun. 7, 1994;91(12):5710–4.

Smith et al., "Oxidative damage in Alzheimer's," *Nature.* Jul. 11, 1996;382(6587):120–1.

Smith et al., "Excess brain protein oxidation and enzyme dysfunction in normal aging and in Alzheimer disease," *Proc Natl Acad Sci U S A.* Dec. 1, 1991;88(23):10540–3.

Subbarao et al., "Autopsy samples of Alzheimer's cortex show increased peroxidation in vitro," *J Neurochem.* Jul. 1990;55(1):342–5.

Svennerholm et al., Membrane lipids, selectively diminished in Alzheimer brains, suggest synapse loss as a primary event in early-onset form (type I) and demyelination in late-onset form (type II), *J Neurochem.* Mar. 1994;62(3):1039–47.

Takahashi et al., "Spontaneous transformation and immortalization of human endothelial cells," *In Vitro Cell Dev Biol.* Mar. 1990;26(3 Pt 1):265–74.

Tsuchiya et al., "In vivo visualization of oxygen radical-dependent photoemission," *Methods Enzymol (Oxygen Radicals in Biological Systems).* 1994;233C:128–40.

Villas et al., "flow cytometry: an overview," *Cell Vis.* Jan.–Feb. 1998;5(1):56–61.

Wells, "Additivity of Mutational Effects in Proteins," (1990) *Biochemistry* 29(37):8509–8517.

Yan et al., "Glycated tau protein in Alzheimer disease: a mechanism for induction of oxidant stress," *Proc Natl Acad Sci U S A.* Aug. 2, 1994;91(16):7787–91.

Zimecki et al., "Effect of a proline–rich polypeptide (PRP) on the development of hemolytic anemia and survival of New Zealand black (NZB) mice," *Arch Immunol Ther Exp (Warsz)*. 1991;39(5–6):461–7.

Cosgaya et al., "Neuronal differentiation of PC12 cells induced by engrailed homeodomain is DNA–binding specific and independent of MAP kinases," *Journal of Cell Science*, 1998; 111: 2377–2384.

Kimball, John W., "White Blood Cells (leukocytes)," *Kimball's Biology Papers* [online]. [retrieved on Dec. 2, 2002]. Retrieved from the internet: <http://users.rcn.com/jkimball.ma.ultranet/BiologyPages/B/Blood.html.>; 2 pgs.

Leszek et al., "Colostrinin™ proline–rich polypeptide compley from ovine colostrum– a long–term study of its efficacy in Alzheimer's disease," *Med Sci Monit.*, 2002;8(10): 193–196.

Vaudry et al., "Signaling Pathways for PC12 Cell Differentiation: Making the Right Connections," *Science* May 31, 2002;296: 1648–1649.

Bikfalvi et al., "Biological Roles of Fibroblast Growth Factor–2," *Endocrine Reviews*, Feb. 1997;18(1): 26–45.

Kandel et al., "Principles of Neural Science," 4$^{th}$ Ed.; 2002: 67–81, 85–86.

Kruzel et al., "Towards an Understanding of Biological Role of Colostrinin Peptides," *Journal of Molecular Neuroscience*, Dec. 2001;17(3): 379–389.

Popik et al., "Cognitive effects of Colostral–Val nonapeptide in aged rats," *Behavioural Brain Research*, Jan. 29, 2001;118(2): 201–208.

Zhen et al., "Lithium regulates protein tyrosine phosphatase activity in vitro and in vivo," *Psychopharmacology*, 2002;162: 379–384.

\* cited by examiner

SEQUENCE LISTING

<160> NUMBER OF SEQ ID NOS: 34

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 1

Met Gln Pro Pro Pro Leu Pro
 1               5

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 2

Leu Gln Thr Pro Gln Pro Leu Leu Gln Val Met Met Glu Pro Gln Gly
 1               5                  10                  15
Asp

<210> SEQ ID NO 3
<211> LENGTH: 18
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 3

Asp Gln Pro Pro Asp Val Glu Lys Pro Asp Leu Gln Pro Phe Gln Val
 1               5                  10                  15
Gln Ser

<210> SEQ ID NO 4
<211> LENGTH: 12
<212> TYPE: PRT
<213> ORGANISM: Artificial Sequence

```
<220> FEATURE:
<223> OTHER INFORMATION: Description of Artificial Sequence:  synthetic
      peptide

<400> SEQUENCE: 4

Leu Phe Phe Phe Leu Pro Val Val Asn Val Leu Pro
  1               5                  10

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 5

Asp Leu Glu Met Pro Val Leu Pro Val Glu Pro Phe Pro Phe Val
  1               5                  10                  15

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 6

Met Pro Gln Asn Phe Tyr Lys Leu Pro Gln Met
  1               5                  10

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 7

Val Leu Glu Met Lys Phe Pro Pro Pro Gln Glu Thr Val Thr
  1               5                  10                  15

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 8

Leu Lys Pro Phe Pro Lys Leu Lys Val Glu Val Phe Pro Phe Pro
  1               5                  10                  15

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 9

Val Val Met Glu Val
  1               5
```

```
<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 10

Ser Glu Gln Pro
  1

<210> SEQ ID NO 11
<211> LENGTH: 3
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 11

Asp Lys Glu
  1

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 12

Phe Pro Pro Pro Lys
  1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 13

Asp Ser Gln Pro Pro Val
  1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 14

Asp Pro Pro Pro Pro Gln Ser
  1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: synthetic
      peptide
```

```
<400> SEQUENCE: 15

Ser Glu Glu Met Pro
 1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 16

Lys Tyr Lys Leu Gln Pro Glu
 1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 17

Val Leu Pro Pro Asn Val Gly
 1               5

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 18

Val Tyr Pro Phe Thr Gly Pro Ile Pro Asn
 1               5                  10

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 19

Ser Leu Pro Gln Asn Ile Leu Pro Leu
 1               5

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 20

Thr Gln Thr Pro Val Val Val Pro Pro Phe
 1               5                  10

<210> SEQ ID NO 21
<211> LENGTH: 18
<212> TYPE: PRT
```

```
<213> ORGANISM: Artificial Sequence
<220> FEATURE:
<223> OTHER INFORMATION: Description of Artificial Sequence: synthetic
      peptide

<400> SEQUENCE: 21

Leu Gln Pro Glu Ile Met Gly Val Pro Lys Val Lys Glu Thr Met Val
 1               5                  10                  15
Pro Lys

<210> SEQ ID NO 22
<211> LENGTH: 18
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 22

His Lys Glu Met Pro Phe Pro Lys Tyr Pro Val Glu Pro Phe Thr Glu
 1               5                  10                  15
Ser Gln

<210> SEQ ID NO 23
<211> LENGTH: 18
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 23

Ser Leu Thr Leu Thr Asp Val Glu Lys Leu His Leu Pro Leu Pro Leu
 1               5                  10                  15
Val Gln

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 24

Ser Trp Met His Gln Pro Pro
 1               5

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 25

Gln Pro Leu Pro Pro Thr Val Met Phe Pro
 1               5                  10

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 26
```

```
Pro Gln Ser Val Leu Ser
  1               5

<210> SEQ ID NO 27
<211> LENGTH: 22
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 27

Leu Ser Gln Pro Lys Val Leu Pro Val Pro Gln Lys Ala Val Pro Gln
  1               5                  10                  15
Arg Asp Met Pro Ile Gln
                 20

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 28

Ala Phe Leu Leu Tyr Gln Glu
  1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 29

Arg Gly Pro Phe Pro Ile Leu Val
  1               5

<210> SEQ ID NO 30
<211> LENGTH: 18
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 30

Ala Thr Phe Asn Arg Tyr Gln Asp Asp His Gly Glu Glu Ile Leu Lys
  1               5                  10                  15
Ser Leu

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 31

Val Glu Ser Tyr Val Pro Leu Phe Pro
  1               5

<210> SEQ ID NO 32
```

-continued

```
<211> LENGTH: 13
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 32

Phe Leu Leu Tyr Gln Glu Pro Val Leu Gly Pro Val Arg
  1               5                  10

<210> SEQ ID NO 33
<211> LENGTH: 3
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 33

Leu Asn Phe
  1

<210> SEQ ID NO 34
<211> LENGTH: 15
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 34

Met His Gln Pro Pro Gln Pro Leu Pro Pro Thr Val Met Phe Pro
  1               5                  10                  15
```

USE OF COLOSTRININ, CONSTITUENT PEPTIDES THEREOF, AND ANALOGS THEREOF, AS OXIDATIVE STRESS REGULATORS

CROSS-REFERENCE TO RELATED APPLICATIONS

This application is a divisional of U.S. application Ser. No. 09/641,803, filed Aug. 17, 2000, now U.S. Pat. No. 6,500,798, which claims priority from U.S. application Ser. No. 60/149,310, filed on Aug. 17, 1999, which is incorporated herein by reference.

BACKGROUND OF THE INVENTION

Colostrum is a component of the milk of mammals during the first few days after birth. Colostrum is a thick yellowish fluid and is the first lacteal secretion post parturition and contains a high concentration of immunogloblins (IgG, IgM, and IgA) and a variety of non-specific proteins. Colostrum also contains various cells such as granular and stromal cells, neutrophils, monocyte/macrophages, and lymphocytes. Colostrum also includes growth factors, hormones, and cytokines. Unlike mature breast milk, colostrum contains low sugar, low iron, but is rich is lipids, proteins, mineral salts, vitamins, and immunoglobins.

Colostrum also includes or contains a proline-rich polypeptide aggregate or complex, which is referred to as colostrinin. One peptide fragment of colostrinin is Val-Glu-Ser-Tyr-Val-Pro-Leu-Phe-Pro (SEQ ID NO:31), which is disclosed in International Publication No. WO-A-98/14473. Colostrinin and this fragment have been identified as useful in the treatment of disorders of the central nervous system, neurological disorders, mental disorders, dementia, neurodegenerative diseases, Alzheimer's disease, motor neurone disease, psychosis, neurosis, chronic disorders of the immune system, diseases with a bacterial and viral aetiology, and acquired immunological deficiencies, as set forth in International Publication No. WO-A-98/14473.

Although certain uses for colostrinin have been identified, it would represent an advancement in the art to discover and disclose other uses for colostrinin, or a component thereof, that are not readily ascertainable from the information currently known about colostrinin or its constituents.

SUMMARY OF THE INVENTION

The present invention relates to the use of colostrinin, at least one constituent (i.e., component) peptide thereof, at least one active analog thereof (e.g., peptide having an N-terminal sequence equivalent to an N-terminal sequence of at least one of the colostrinin constituent peptides), and combinations thereof, as an oxidative stress regulator. These oxidative stress regulators can be used in vitro or in vivo, including internal and external use in animals including mammals such as humans. They can be used for preventative (i.e., prophylactic) treatments or for therapeutic treatments.

In one embodiment, the present invention provides a method for modulating (e.g., regulating or adjusting) the oxidative stress level in a cell. The method includes contacting the cell with an oxidative stress regulator selected from the group of colostrinin, a constituent peptide thereof, an active analog thereof, and combinations thereof, under conditions effective to change (decrease or increase, but preferably, decrease) or prevent an increase in the level of an oxidizing species in the cell. By this it is meant that no increase or any amount of change (preferably, a decrease) in the level of one or more oxidizing species are within the scope of the invention, although not all oxidizing species monitored would necessarily have to demonstrate a change (preferably, decrease) or lack of an increase in its level. The cell can be in a cell culture, a tissue, an organ, or an organism. Hence, this method can be carried out in vivo or in vitro.

In another embodiment, the present invention provides a method for modulating the oxidative stress level in a patient. The method includes administering to the patient an oxidative stress regulator selected from the group of colostrinin, a constituent peptide thereof, an active analog thereof, and combinations thereof, under conditions effective to decrease or prevent an increase in the level of an oxidizing species in the patient. By this it is meant that no increase or any amount of change (increase or decrease, but preferably, a decrease) in the level of one or more oxidizing species are within the scope of the invention, although not all oxidizing species monitored would necessarily have to demonstrate a decrease or lack of an increase in its level.

Yet another method of the invention is a method of modulating the oxidative stress level of the skin of a patient, and preferably, treating (prophylactically or therapeutically) oxidative damage to the skin of a patient. The method includes applying to skin a topical formulation (e.g., sun screen) that includes an oxidative stress regulator selected from the group of colostrinin, a constituent peptide thereof, an active analog thereof, and combinations thereof, under conditions effective to change (increase or decrease, but preferably, decrease) or prevent an increase in the level of damage to a biomolecule of the patient. By this it is meant that no increase or any amount of change (increase or decrease, but preferably, decrease) in the level or damage to one or more biomolecules are within the scope of the invention, although not all biomolecules monitored would necessarily have to demonstrate a decrease or lack of an increase in its level of damage. The biomolecule may be selected from the group of a DNA, a protein, a lipid, or combinations thereof.

In other embodiments, the invention provides the use of an oxidative stress regulator in the manufacture of a medicament for use in the methods described herein.

A further embodiment of the invention is a cosmetic formulation that includes an oxidative stress regulator selected from the group of colostrinin, a constituent peptide thereof, an active analog thereof, and combinations thereof.

As used herein, "a" or "an" means one or more (or at least one), such that combinations of active agents (i.e., active oxidative stress regulators), for example, can be used in the compositions and methods of the invention. Thus, a composition that includes "a" polypeptide refers to a composition that includes one or more polypeptides.

"Amino acid" is used herein to refer to a chemical compound with the general formula: $NH_2$—CRH—COOH, where R, the side chain, is H or an organic group. Where R is organic, R can vary and is either polar or nonpolar (i.e., hydrophobic). The amino acids of this invention can be naturally occurring or synthetic (often referred to as nonproteinogenic). As used herein, an organic group is a hydrocarbon group that is classified as an aliphatic group, a cyclic group or combination of aliphatic and cyclic groups. The term "aliphatic group" means a saturated or unsaturated linear or branched hydrocarbon group. This term is used to encompass alkyl, alkenyl, and alkynyl groups, for example. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" refers to mono- or polycyclic aromatic hydrocarbon groups. As used herein, an organic group can be substituted or unsubstituted.

The terms "polypeptide" and "peptide" are used interchangeably herein to refer to a polymer of amino acids. These terms do not connote a specific length of a polymer of amino acids. Thus, for example, the terms oligopeptide, protein, and enzyme are included within the definition of polypeptide or peptide, whether produced using recombinant techniques, chemical or enzymatic synthesis, or naturally occurring. This term also includes polypeptides that have been modified or derivatized, such as by glycosylation, acetylation, phosphorylation, and the like.

The following abbreviations are used throughout the application:

| | |
|---|---|
| A = Ala = Alanine | T = Thr = Threonine |
| V = Val = Valine | C = Cys = Cysteine |
| L = Leu = Leucine | Y = Tyr = Tyrosine |
| I = Ile = Isoleucine | N = Asn = Asparagine |
| P = Pro = Proline | Q = Gln = Glutamine |
| F = Phe = Phenylalanine | D = Asp = Aspartic Acid |
| W = Trp = Tryptophan | E = Glu = Glutamic Acid |
| M = Met = Methionine | K = Lys = Lysine |
| G = Gly = Glycine | R = Arg = Arginine |
| S = Ser = Serine | H = His = Histidine |

BRIEF DESCRIPTION OF THE DRAWINGS

The invention can be better understood with reference to the following detailed description together with the appended illustrative drawings in which like elements are numbered the same.

DETAILED DESCRIPTION OF PREFERRED EMBODIMENTS OF THE INVENTION

Figure 1A:
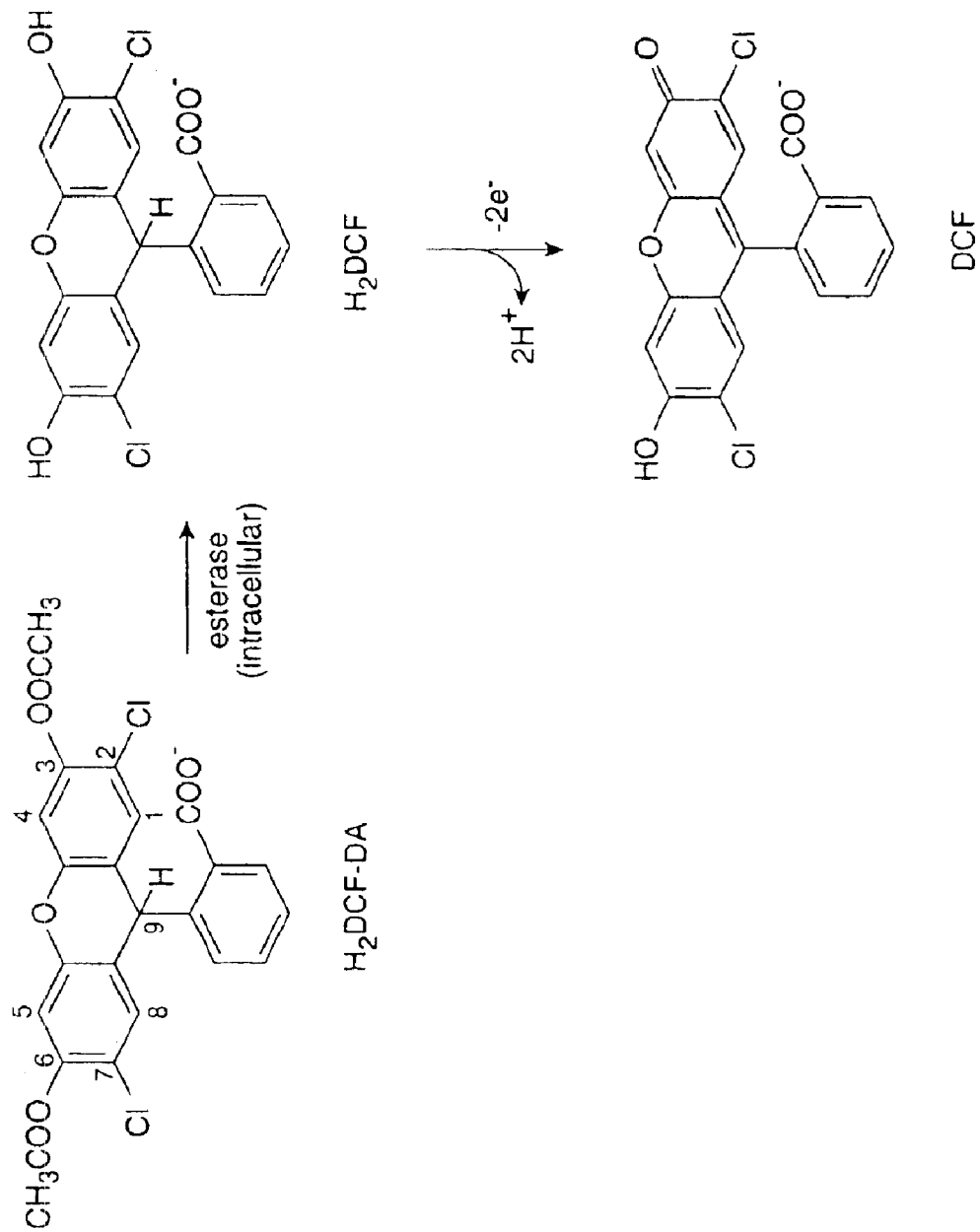
FIGS. 1A, 1B and 1C. Principle of 2',7'-dihydro-dichlorofluorescein-diacetate assay. Chemical structure of $H_2$DCF-DA, $H_2$DCF and DCF (A). Uptake of $H_2$DCF-DA and fate of intracellular $H_2$DCF (B). Histogram: a change in DCF-mediated fluorescence intensity after treatment of $H_2$DCF-loaded cells with 50 $\mu$M $H_2O_2$ (C).

The inventors have found that colostrinin, at least one constituent peptide thereof, and/or at least one active analog thereof (e.g., a peptide having an N-terminal sequence equivalent to an N-terminal sequence of at least one of the colostrinin constituent peptides) can be used as general purpose oxidative stress regulator for use in vitro and in vivo, including for internal and external use in animals including mammals such as humans. Such oxidative stress regulators are referred to herein as "active agents." Significantly, such oxidative stress regulators can be administered alone or in various combinations to a patient (e.g., animals including humans) as a medication or dietary (e.g., nutrient) supplement in a dose sufficient to modulate the oxidative stress level throughout the patient's body, in a specific tissue site, or in a collection of tissues (organs). Alternatively, they can be administered topically to reduce the effects of environmental- and oxidative stress-induced aging of the skin and to improve dermal appearance and youthfulness.

Reactive oxidizing species include superoxide, hydroxyl radicals, hydrogen peroxide, lipid peroxyl, oxoperoxinitrate, among others. Many of these are required for normal cell functions, but when present in excess, cells can become oxidatively stressed. Oxidative stress causes cellular damage, resulting in alteration of the redox state (e.g., depletion of nucleotide coenzymes and disturbance of sulfhydryl-containing enzymes), and saturation and destruction of the antioxidant defense and DNA repair system. If the cellular balance of the level of oxidizing species (e.g., reactive oxygen species and reactive nitrogen species) is not restored, several pathological processes are elicited, including DNA damage, lipid peroxidation, loss of intracellular calcium homeostasis, and alteration in cellular signaling and metabolic pathways. In addition, reactive oxidizing species may serve as intracellular messengers in gene regulatory and signal transduction pathways at cellular level. For example, alterations in oxidative metabolism have long been known to result in protein-protein and protein-DNA interactions, consequently reactive oxidizing species are important in the regulation of promoter activities (gene regulation), and more complex cellular processes.

The compositions described herein can be utilized to modulate oxidative stress that can occur in a wide variety of situations. For example, they can be utilized to modulate oxidative stress during/after a premature birth, during/after a normal birth, as well as preventing/delaying aging in a patient. The present invention is advantageous in that modulating oxidative stress can result in enhanced wound healing, as well as the reduction and/or elimination of side effects of cosmetic procedures. Modulating oxidative stress can also result in enhanced repair, regeneration, and/or replacement, of cells, tissues, and/or organs (e.g., kidneys, liver, pancreas, skin, and other internal and external organs) either in vitro or in vivo, as well as enhanced preservation of such organs for transplantation, implantation, or scientific research.

In a preferred embodiment, the present invention provides a method for modulating the oxidative stress level in a cell. The method includes contacting the cell with an active agent under conditions effective to change (either to increase or decrease, but preferably, to decrease) or prevent an increase in the level of at least one oxidizing species in the cell (relative to the same cell under the same conditions without the oxidative stress regulator). The cell can be in a cell culture, a tissue, an organ, or an organism. Hence, the method can be carried out in vitro or in vivo. The cell can be a mammalian cell, and preferably a human cell. In another preferred embodiment, the present invention provides a method for modulating the oxidative stress level in a patient. The method includes administering to the patient an active agent under conditions effective to change (increase or decrease, but preferably, decrease) or prevent an increase in the level of at least one oxidizing species in the patient (relative to the same conditions without the oxidative stress regulator).

The level of oxidative stress in a cell, for example, can be determined by the level of oxidizing species present, which can be determined by evaluating the abundance of oxidized molecules. For an in vitro and in vivo method, the level of at least one oxidizing species (and typically the level of all oxidizing species) in a cell or body fluid, for example, can be determined by the previously published method disclosed in R. B. Singh et al., *Am. J. Cardiol.*, 76, 1233–1238 (1995). The level of increase or decrease in oxidizing activity is typically determined by comparison to a cell or other sample that has not been contacted with a composition described herein. Specific in vitro methods are described in the Examples Section.

Yet another method of the invention is a method of modulating the oxidative stress level of the skin of a patient, and preferably treating (prophylactically or therapeutically) oxidative damage to the skin of a patient. The method includes applying to skin a topical formulation (e.g., sun screen) that includes an active agent under conditions effective to change (increase or decrease, but preferably decrease) or prevent an increase in the level of damage to a biomolecule of the patient, such as a DNA, a protein, and/or a lipid. The level of oxidative damage to the skin of a patient can be determined by the level of protein oxidation using western blot immunoassays according to the method of E. Shacter et al., *Free Radic. Biol. Med.*, 17, 429–437 (1994), the level of oxidative damage to DNA using a DNA binding assay according to the method of I. A. Bespalov et al., *J. Mol. Biol.*, 293, 1085–1095 (1999), and the level of oxidative modification of lipids as described by H. Esterbauer et al., *Free Radic. Biol. Med.*, 11, 81–128 (1991).

Colostrinin is composed of peptides, the aggregate of which has a molecular weight range between about 5.8 to about 26 kiloDaltons (kDa) determined by polyacrylamide gel electrophoresis. It has a greater concentration of proline than any other amino acid. Ovine colostrinin has been found to have a molecular weight of about 18 kDa and includes three non-covalently linked subunits having a molecular weight of about 6 kDa and has about 22 wt-% proline. Ovine colostrinin has also been shown to contain the following number of residues per subunit: lysine-2; histidine-1; arginine-0; aspartic acid-2; threonine-4; serine-3; glutamic acid-6; proline-11; glycine-2; alanine-0; valine-5; methionine-2; isoleucine-2; leucine-6; tyrosine-1; phenylalanine-3; and cysteine-0.

Colostrinin has been found to include a number of peptides ranging from 3 amino acids to 22 amino acids or more. These can be obtained by various known techniques, including isolation and purification involving eletrophoresis and synthetic techniques. The specific method of obtaining colostrinin and SEQ ID NO:31 is described in International Publication No. WO-A-98/14473. Using HPLC and Edelman Degradation, over 30 constituent peptides of colostrinin have been identified, which can be classified into several groups: (A) those of unknown precursor; (B) those having a β-casein homologue precursor; (C) those having a β-casein precursor; and (D) those having an annexin precursor. These peptides are described in International Patent Publication No. WO 00/75173, filed Jun. 2, 2000, claiming priority to Jun. 2, 1999, and can be synthesized according to the general method described in the Examples Section. These peptides (i.e., constituent peptides of colostrinin), which can be derived from colostrinin or chemically synthesized, include: MQPPPLP (SEQ ID NO:1); LQTPQPLLQVMMEPQGD (SEQ ID NO:2); DQPPDVEKPDLQPFQVQS (SEQ ID NO:3); LFFFLPVVNVLP (SEQ ID NO:4); DLEMPVLPVEPFPFV (SEQ ID NO:5); MPQNFYKLPQM (SEQ ID NO:6); VLEMKFPPPPQETVT (SEQ ID NO:7); LKPFPKLKVEVFPFP (SEQ ID NO:8); VVMEV (SEQ ID NO:9); SEQP (SEQ ID NO:10); DKE (SEQ ID NO:11); FPPPK (SEQ ID NO:12); DSQPPV (SEQ ID NO:13); DPPPPQS (SEQ ID NO:14); SEEMP (SEQ ID NO:15); KYKLQPE (SEQ ID NO:16); VLPPNVG (SEQ ID NO:17); VYPFTGPIPN (SEQ ID NO:18); SLPQNILPL (SEQ ID NO:19); TQTPVVVPPF (SEQ ID NO:20); LQPEIMGVPKVKETMVPK (SEQ ID NO:21); HKEMPFPKYPVEPFTESQ (SEQ ID NO:22); SLTLTDVEKLHLPLPLVQ (SEQ ID NO:23); SWMHQPP (SEQ ID NO:24); QPLPPTVMFP (SEQ ID NO:25); PQSVLS (SEQ ID NO:26); LSQPKVLPVPQKAVPQRDMPIQ (SEQ ID NO:27); AFLLYQE (SEQ ID NO:28); RGPFPILV (SEQ ID NO:29); ATFNRYQDDHGEEILKSL (SEQ ID NO:30); VESYVPLFP (SEQ ID NO:31); FLLYQEPVLGPVR (SEQ ID NO:32); LNF (SEQ ID NO:33); and MHQPPQPLPPTVMFP (SEQ ID NO:34). These can be classified as follows: (A) those of unknown precursor include SEQ ID NOs:2, 6, 7, 8, 10, 11, 14, and 33; (B) those having a β-casein homologue precursor include SEQ ID NOs:1, 3, 4, 5, 9, 12, 13, 15, 16, 17, and 31; (C) those having a β-casein precursor include SEQ ID NOs:18 (casein amino acids 74–83), 19 (casein amino acids 84–92), 20 (casein amino acids 93–102), 21 (casein amino acids 103–120), 22 (casein amino acids 121–138), 23 (casein amino acids 139–156), 24 (casein amino acids 157–163), 25 (casein amino acids 164–173), 26 (casein amino acids 174–179), 27 (casein amino acids 180–201), 28 (casein amino acids 202–208), 29 (casein amino acids 214–222), 32 (casein amino acids 203–214), and 34 (casein amino acids 159–173); and (D) those having an annexin precursor include SEQ ID NO:30 (annexin amino acids 203–220).

A preferred group of such peptides includes: MQPPPLP (SEQ ID NO:1); LQTPQPLLQVMMEPQGD (SEQ ID NO:2); DQPPDVEKPDLQPFQVQS (SEQ ID NO:3); LFF-FLPVVNVLP (SEQ ID NO:4); DLEMPVLPVEPFPFV (SEQ ID NO:5); MPQNFYKLPQM (SEQ ID NO:6); VLEMKFPPPPQETVT (SEQ ID NO:7); LKPF-KLKVEVFPFP (SEQ ID NO:8); and combinations thereof.

The polypeptides of SEQ ID NOs: 1–34 can be in their free acid form or they can be amidated at the C-terminal carboxylate group. The present invention also includes analogs of the polypeptides of SEQ ID NOs: 1–34, which includes polypeptides having structural similarity with SEQ ID NOs: 1–34. These peptides can also form a part of a larger peptide. An "analog" of a polypeptide includes at least a portion of the polypeptide, wherein the portion contains deletions or additions of one or more contiguous or non-contiguous amino acids, or containing one or more amino acid substitutions. An "analog" can thus include additional amino acids at one or both of the terminii of the polypeptides listed above. Substitutes for an amino acid in the polypeptides of the invention are preferably conservative substitutions, which are selected from other members of the class to which the amino acid belongs. For example, it is well-known in the art of protein biochemistry that an amino acid belonging to a grouping of amino acids having a particular size or characteristic (such as charge, hydrophobicity and hydrophilicity) can generally be substituted for another amino acid without substantially altering the structure of a polypeptide.

For the purposes of this invention, conservative amino acid substitutions are defined to result from exchange of amino acids residues from within one of the following classes of residues: Class I: Ala, Gly, Ser, Thr, and Pro (representing small aliphatic side chains and hydroxyl group side chains); Class II: Cys, Ser, Thr and Tyr (representing side chains including an —OH or —SH group); Class III: Glu, Asp, Asn and Gln (carboxyl group containing side chains): Class IV: His, Arg and Lys (representing basic side chains); Class V: Ile, Val, Leu, Phe and Met (representing hydrophobic side chains); and Class VI: Phe, Trp, Tyr and His (representing aromatic side chains). The classes also include related amino acids such as 3Hyp and 4Hyp in Class I; homocysteine in Class II; 2-aminoadipic acid, 2-aminopimelic acid, γ-carboxyglutamic acid, β-carboxyaspartic acid, and the corresponding amino acid amides in Class III; ornithine, homoarginine, N-methyl lysine, dimethyl lysine, trimethyl lysine, 2,3-diaminopropionic acid, 2,4-diaminobutyric acid, homoarginine, sarcosine and hydroxylysine in Class IV; substituted phenylalanines, norleucine, norvaline, 2-aminooctanoic acid, 2-aminoheptanoic acid, statine and β-valine in Class V; and naphthylalanines, substituted phenylalanines, tetrahydroisoquinoline-3-carboxylic acid, and halogenated tyrosines in Class VI.

Preferably, the active analogs of colostrinin and its constituent peptides include polypeptides having a relatively large number of proline residues. Because proline is not a common amino acid, a "large number" preferably means that a polypeptide includes at least about 15% proline (by number), and more preferably at least about 20% proline (by number). Most preferably, active analogs include more proline residues than any other amino acid.

As stated above, active analogs of colostrinin and its constituent peptides include polypeptides having structural similarity. Structural similarity is generally determined by aligning the residues of the two amino acid sequences to optimize the number of identical amino acids along the lengths of their sequences; gaps in either or both sequences are permitted in making the alignment in order to optimize the number of identical amino acids, although the amino acids in each sequence must nonetheless remain in their proper order. Preferably, two amino acid sequences are compared using the Blastp program, version 2.0.9, of the BLAST 2 search algorithm, available at on the worldwide web at ncbi.nlm.nih.gov/gorf/bl2.html. Preferably, the default values for all BLAST 2 search parameters are used, including matrix=BLOSUM62; open gap penalty=11, extension gap penalty=1, gap x_dropoff=50, expect=10, wordsize=3, and filter on. In the comparison of two amino acid sequences using the BLAST search algorithm, structural similarity is referred to as "identity." Preferably, an active analog of colostrinin or its constituent peptides has a structural similarity to colostrinin or one or more of its constituent peptides (preferably, one of SEQ ID NOs: 1–34) of at least about 70% identity, more preferably, at least about 80% identity, and most preferably, at least about 90% identity.

Colostrinin or any combination of its peptide components or active analogs thereof can be derived (preferably, isolated and purified) naturally such as by extraction from colostrum or can be synthetically constructed using known peptide polymerization techniques. For example, the peptides of the invention may be synthesized by the solid phase method using standard methods based on either t-butyloxycarbonyl (BOC) or 9-fluorenylmethoxy-carbonyl (FMOC) protecting groups. This methodology is described by G. B. Fields et al. in Synthetic Peptides: A User's Guide, W. M. Freeman & Company, New York, N.Y., pp. 77–183 (1992). Moreover, gene sequence encoding the colostrinin peptides or analogs thereof can be constructed by known techniques such as expression vectors or plasmids and transfected into suitable microorganisms that will express the DNA sequences thus preparing the peptide for later extraction from the medium in which the microorganism are grown. For example, U.S. Pat. No. 5,595,887 describes methods of forming a variety of relatively small peptides through expression of a recombinant gene construct coding for a fusion protein which includes a binding protein and one or more copies of the desired target peptide. After expression, the fusion protein is isolated and cleaved using chemical and/or enzymatic methods to produce the desired target peptide.

The peptides used in the methods of the present invention may be employed in a monovalent state (i.e., free peptide or a single peptide fragment coupled to a carrier molecule). The peptides may also be employed as conjugates having more than one (same or different) peptide fragment bound to a single carrier molecule. The carrier may be a biological carrier molecule (e.g., a glycosaminoglycan, a proteoglycan, albumin or the like) or a synthetic polymer (e.g., a polyalkyleneglycol or a synthetic chromatography support). Typically, ovalbumin, human serum albumin, other proteins, polyethylene glycol, or the like are employed as the carrier. Such modifications may increase the apparent affinity and/or change the stability of a peptide. The number of peptide fragments associated with or bound to each carrier can vary, but from about 4 to 8 peptides per carrier molecule are typically obtained under standard coupling conditions.

For instance, peptide/carrier molecule conjugates may be prepared by treating a mixture of peptides and carrier molecules with a coupling agent, such as a carbodiimide. The coupling agent may activate a carboxyl group on either the peptide or the carrier molecule so that the carboxyl group can react with a nucleophile (e.g., an amino or hydroxyl group) on the other member of the peptide/carrier molecule, resulting in the covalent linkage of the peptide and the carrier molecule. For example, conjugates of a peptide coupled to ovalbumin may be prepared by dissolving equal amounts of lyophilized peptide and ovalbumin in a small volume of water. In a second tube, 1-ethyl-3-(3-dimethylamino-propyl)-carbodiimide hydrochloride (EDC; ten times the amount of peptide) is dissolved in a small amount of water. The EDC solution was added to the peptide/ovalbumin mixture and allowed to react for a number of hours. The mixture may then dialyzed (e.g., into phosphate buffered saline) to obtain a purified solution of peptide/ovalbumin conjugate. Peptide/carrier molecule conjugates prepared by this method typically contain about 4 to 5 peptides per ovalbumin molecule.

The present invention also provides a composition that includes one or more active agents (i.e., colostrinin, at least one constituent peptide thereof, or active analog thereof) of the invention and one or more carriers, preferably a pharmaceutically acceptable carrier. The methods of the invention include administering to, or applying to the skin of, a patient, preferably a mammal, and more preferably a human, a composition of the invention in an amount effective to produce the desired effect. The active agents of the present invention are formulated for enteral administration (oral, rectal, etc.) or parenteral administration (injection, internal pump, etc.). The administration can be via direct injection into tissue, interarterial injection, intervenous injection, or other internal administration procedures, such as through the use of an implanted pump, or via contacting the composition with a mucus membrane in a carrier designed to facilitate transmission of the composition across the mucus membrane such as a suppository, eye drops, inhaler, or other similar administration method or via oral administration in the form of a syrup, a liquid, a pill, capsule, gel coated tablet, or other similar oral administration method. The active agents can be incorporated into an adhesive plaster, a patch, a gum, and the like, or it can be encapsulated or incorporated into a bio-erodible matrix for controlled release.

The carriers for internal administration can be any carriers commonly used to facilitate the internal administration of compositions such as plasma, sterile saline solution, IV solutions or the like. Carriers for administration through mucus membranes can be any well-known in the art. Carriers for administration oral can be any carrier well-known in the art.

The formulations may be conveniently presented in unit dosage form and may be prepared by any of the methods well known in the art of pharmacy. All methods include the step of bringing the active agent into association with a carrier which constitutes one or more accessory ingredients. In general, the formulations are prepared by uniformly and intimately bringing the active agent into association with a liquid carrier, a finely divided solid carrier, or both, and then, if necessary, shaping the product into the desired formulations.

Formulations suitable for parenteral administration conveniently include a sterile aqueous preparation of the active agent, or dispersions of sterile powders of the active agent, which are preferably isotonic with the blood of the recipient. Isotonic agents that can be included in the liquid preparation include sugars, buffers, and sodium chloride. Solutions of the active agent can be prepared in water, optionally mixed with a nontoxic surfactant. Dispersions of the active agent can be prepared in water, ethanol, a polyol (such as glycerol, propylene glycol, liquid polyethylene glycols, and the like), vegetable oils, glycerol esters, and mixtures thereof. The ultimate dosage form is sterile, fluid, and stable under the conditions of manufacture and storage. The necessary fluidity can be achieved, for example, by using liposomes, by employing the appropriate particle size in the case of dispersions, or by using surfactants. Sterilization of a liquid preparation can be achieved by any convenient method that preserves the bioactivity of the active agent, preferably by filter sterilization. Preferred methods for preparing powders include vacuum drying and freeze drying of the sterile injectable solutions. Subsequent microbial contamination can be prevented using various antimicrobial agents, for example, antibacterial, antiviral and antifungal agents including parabens, chlorobutanol, phenol, sorbic acid, thimerosal, and the like. Absorption of the active agents over a prolonged period can be achieved by including agents for delaying, for example, aluminum monostearate and gelatin.

Formulations of the present invention suitable for oral administration may be presented as discrete units such as tablets, troches, capsules, lozenges, wafers, or cachets, each containing a predetermined amount of the active agent as a powder or granules, as liposomes containing the active agent, or as a solution or suspension in an aqueous liquor or non-aqueous liquid such as a syrup, an elixir, an emulsion, or a draught. The amount of active agent is such that the dosage level will be effective to produce the desired result in the subject.

Nasal spray formulations include purified aqueous solutions of the active agent with preservative agents and isotonic agents. Such formulations are preferably adjusted to a pH and isotonic state compatible with the nasal mucous membranes. Formulations for rectal or vaginal administration may be presented as a suppository with a suitable carrier such as cocoa butter, or hydrogenated fats or hydrogenated fatty carboxylic acids. Ophthalmic formulations are prepared by a similar method to the nasal spray, except that the pH and isotonic factors are preferably adjusted to match that of the eye. Topical formulations include the active agent dissolved or suspended in one or more media such as mineral oil, DMSO, polyhydroxy alcohols, or other bases used for topical pharmaceutical formulations.

Useful dosages of the active agents can be determined by comparing their in vitro activity and the in vivo activity in animal models. Methods for extrapolation of effective dosages in mice, and other animals, to humans are known in the art; for example, see U.S. Pat. No. 4,938,949.

The tablets, troches, pills, capsules, and the like may also contain one or more of the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, fructose, lactose or aspartame; and a natural or artificial flavoring agent. When the unit dosage form is a capsule, it may further contain a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, or sugar and the like. A syrup or elixir may contain one or more of a sweetening agent, a preservative such as methyl- or propylparaben, an agent to retard crystallization of the sugar, an agent to increase the solubility of any other ingredient, such as a polyhydric alcohol, for example glycerol or sorbitol, a dye, and flavoring agent. The material used in preparing any unit dosage form is substantially nontoxic in the amounts employed. The active agent may be incorporated into sustained-release preparations and devices.

In a particularly preferred embodiment, the active agents of the present invention can be used in cosmetic formulations (e.g., skincare cream, sunscreen, decorative make-up products, and other dermatological compositions) in various pharmaceutical dosage forms, and especially in the form of oil-in-water or water-in-oil emulsions, solutions, gels, or vesicular dispersions. The cosmetic formulations may take the form of a cream which can be applied either to the face or to the scalp and hair, as well as to the human body. They can also serve as a base for a lipstick.

Particularly preferred cosmetic formulations can also include additives such as are usually used in such formulations, for example preservatives, bactericides, perfumes, antifoams, dyes, pigments which have a coloring action, surfactants, thickeners, suspending agents, fillers, moisturizers and/or humectants, fats, oils, waxes or other customary constituents of a cosmetic formulation, such as alcohols, polyols, polymers, foam stabilizers, electrolytes, organic solvents, or silicone derivatives.

Cosmetic formulations typically include a lipid phase and often an aqueous phase. The lipid phase can advantageously be chosen from the following group of substances: mineral oils, mineral waxes oils, such as triglycerides of capric or of caprylic acid, but preferably castor oil; fats, waxes and other natural and synthetic fatty substances, preferably esters of fatty acids with alcohols of low C number, for example with isopropanol, propylene glycol or glycerol, or esters of fatty alcohols with alkanoic acids of low C number or with fatty acids; alkyl benzoates; silicone oils, such as dimethylpolysiloxanes, diethylpolysiloxanes, diphenylpolysiloxanes and mixed forms thereof.

If appropriate, the aqueous phase of the formulations according to the invention advantageously includes alcohols, diols or polyols of low C number and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, furthermore alcohols of low C number, for example ethanol, isopropanol, 1,2-propanediol and glycerol, and, in particular, one or more thickeners, which can advantageously be chosen from the group consisting of silicon dioxide, aluminum silicates, polysaccharides and derivatives thereof, for example hyaluronic acid, xanthan gum and hydroxypropylmethylcellulose, particularly advantageously from the group consisting of poly-acrylates, preferably a polyacrylate from the group consisting of so-called Carbopols, for example Carbopols of types 980, 981, 1382, 2984 and 5984, in each case individually or in combination.

A preferred cosmetic formulation is a sunscreen composition. A sunscreen can advantageously additionally include at least one further UVA filter and/or at least one further UVB filter and/or at least one inorganic pigment, preferably an inorganic micropigment. The UVB filters can be oil-soluble or water-soluble. Advantageous oil-soluble UVB filter substances are, for example: 3-benzylidenecamphor derivatives, preferably 3-(4-methylbenzylidene)camphor and 3-benzylidenecamphor; 4-aminobenzoic acid derivatives, preferably 2-ethylhexyl 4-(dimethylamino) benzoate and amyl 4-(dimethylamino)benzoate; esters of cinnamic acid, preferably 2-ethylhexyl 4-methoxycinnamate and isopentyl 4-methoxycinnamate; derivatives of benzophenone, preferably 2-hydroxy-4-methoxybenzophenone, 2-hydroxy-4-methoxy-4'-methylbenzophenone and 2,2'-dihydroxy-4-methoxybenzophenone; esters of benzalmalonic acid, preferably di(2-ethylhexyl) 4-methoxybenzalmalonate. Advantageous water-soluble UVB filter substances are, for example: salts of 2-phenylbenzimidazole-5-sulphonic acid, such as its sodium, potassium or its triethanolammonium salt, and the sulphonic acid itself; sulphonic acid derivatives of benzophenones, preferably 2-hydroxy-4-methoxybenzophenone-5-sulphonic acid and salts thereof; sulphonic acid derivatives of 3-benzylidenecamphor, such as, for example, 4-(2-oxo-3-bornylidenemethyl) benzenesulphonic acid, 2-methyl-5-(2-oxo-3-bornylidenemethyl) benzenesulphonic acid and salts thereof. The list of further UVB filters mentioned which can be used in combination with the active agent(s) according to the invention is not of course intended to be limiting.

EXAMPLES

The invention will be further described by reference to the following detailed examples. The examples are meant to provide illustration and should not be construed as limiting the scope of the present invention.

Materials and Experimental Procedures

Preparation of Peptides:

1. Wash pre-loaded resin with DMF (dimethylformamide), then drain completely.
2. Add 10 ml of 20% piperidine/DMF to resin. Shake for 5 minutes, then drain.
3. Add another 10 ml of 20% piperidine/DMF. Shake for 30 minutes.
4. Drain reaction vessel and wash resin with DMF four times. Then wash once with DCM (dichloromethanol). Check beads using the ninhydrin test—the beads should be blue.
5. The coupling step was carried out as follows:
   a. Prepare the following solution: 1 mmole Fmoc (i.e. fluorenylmethyloxycarbonyl) amino acid 2.1 ml of 0.45 M HBTU/HOBT (1 mmol) (2-(1H-benzotriazol-1-yl)-1,1,3,3-tetramethyluronium hexafluorophosphate/N-hydroxybenzotriazole-$H_2O$) 348 $\mu$l of DIEA (2 mmol) (diisopropylethylamine); and
   b. Add the solution to the resin and shake for a minimum of 30 minutes.
6. Drain reaction vessel and wash the resin again with DMF four times and with DCM once.
7. Perform the ninhydrin test: If positive (no colour)—proceed to step 2 and continue synthesis; If negative (blue colour)—return to step 5 and recouple the same Fmoc amino acid.
8. After the synthesis was complete, the peptide was cleaved from the resin with 5% $H_2O$, 5% phenol, 3% Thionisole, 3% EDT (ethanedithiol), 3% triisopropylsilane and 81% TFA for 2 hours.
9. After 2 hours, filter into cold MTBE (methyl t-butyl ether). The precipitated peptide was then washed twice with cold MTBE and dried under nitrogen gas.
10. The molecular weight of the synthesized peptides was checked by Matrix-Assisted Laser Desorption Time-of-Flight Mass Spectroscopy (LDMS), and the purity was checked by HPLC using a C-18, 300 Angstrom, 5 $\mu$m column.

Cell lines: PC12 cell line derived from medullary pheochromocytoma cells and immortalized human endothelial cells (ECV304: developed from the umbilical vein; K. Takahashi et al., *In Vitro Cell Dev. Biol.* 26, 265–274, 1990) were used to undertake studies described bellow. PC12 cells were obtained from the American Type Culture Collection. ECV304 cells were kindly provided by Dr. Goto (Patology Division, National Cancer Institute, Tokyo, Japan).

Cell culture conditions: PC12 and ECV304 cells were cultured in RPMI-1640 and M199 medium (Gibco-BRL, Life Technologies, Inc., Rockville, Md.), respectively. The media were supplemented with 10% fetal bovine serum (Hyclone Laboratories Inc., Logan, Utah), penicillin (100 U/ml) and streptomycin (100 µg/ml). To evaluate the oxidative stress regulatory activity of colostrinin and constituent peptides, cells were harvested at 70% confluence (log phase).

Figure 1B:
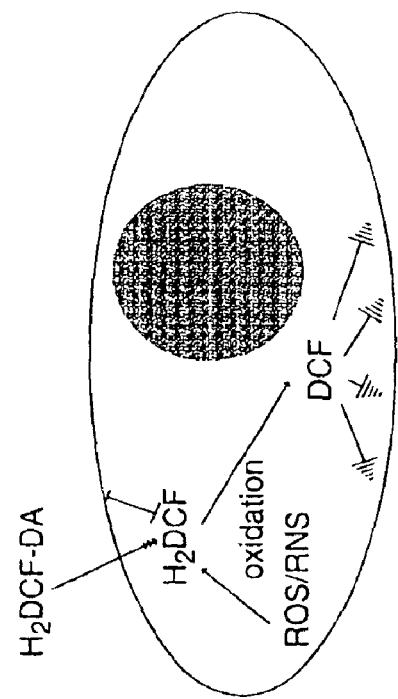

Flow cytometry: Fluorogenic, chemiluminescent, or chromogenic probes have been used extensively to monitor oxidative activity in cells. One of the most popular approaches involves the use of chemically reduced forms (nonfluorescent) of dyes such as fluorescein. After reaction with oxidizing species, these reduced compounds, which are poor fluorescers are oxidized resulting in a dramatic increase in fluorescence intensity. The use of 2'-7'-dichlorofluorescin ($H_2DCF$) for this purpose is shown in FIG. 1A. $H_2DCF$-DA is added to cells, where it diffuses across the cell membrane and is hydrolyzed by intracellular esterases to $H_2DCF$, which upon oxidation, yields the highly fluorescent DCF (FIG. 1B). Oxidation may be achieved by reaction with $H_2O_2$ in the presence of peroxidase, cytochrome c, or $Fe^{2+}$. $H_2DCF$ may also be oxidized by peroxynitrite, superoxide and nitric oxide (M. Tsuchiya et al., *Methods Enzymol.*, 233, 128–140 (1994); C. P. LeBel et al., *Chem. Res. Toxicol.*, 5, 227–231 (1992); G. Rothe et al., *J. Leukoc. Biol.*, 47, 440–448 (1990); J. A. Royall et al., *Arch. Biochem. Biophys.*, 302, 348–355 (1993); and N. W. Kooy et al., *Free Radic. Res.*, 27, 245–254 (1997).

Figure 1C:
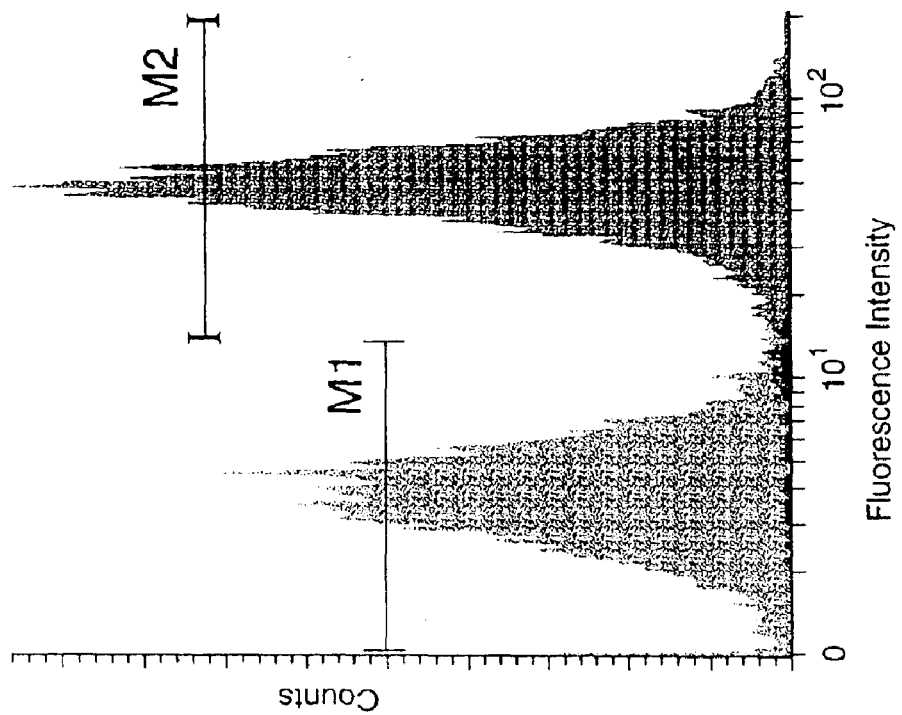

Cells were ($10^6$ cells per ml) loaded with $H_2DCF$-DA (final concentration of 2.5 µM) for 2 min and treated for 10 min with increasing concentrations of individual constituent peptides, colostrinin or colostrum. $H_2DCF$-DA/constituent peptides-treated cells were exposed to $H_2O_2$ (25 µM) and a change in fluorescence intensity were determined as a function of time by flow cytometry. As a control, $H_2DCF$-DA-loaded cells in parallel were treated with $H_2O_2$ (12.5, 25, 50 µM) alone. A typical histogram is shown in FIG. 1C. In additional control experiments antioxidants N-acetyl-L-cysteine and butylated hydroxyanisole were used. All assays were carried out in phenol red-free media, containing 1% fetal bovine serum and 10 mM HEPES (pH: 7.4).

Flow cytometry was performed on a FACScan flow cytometer (Becton Dickinson). The excitation and emission wavelength were 485 nanometers (nm) and 530 nm, respectively. Instrument calibration was performed daily using Calibrate Beads (BDIS) according to the recommendation of the manufacturer (Becton Dickinson). Each sample was run in the setup mode until a cell acquisition gate was established, at which point only events in this gate were acquired. 10,000 events were collected in all studies.

Figure 2B:
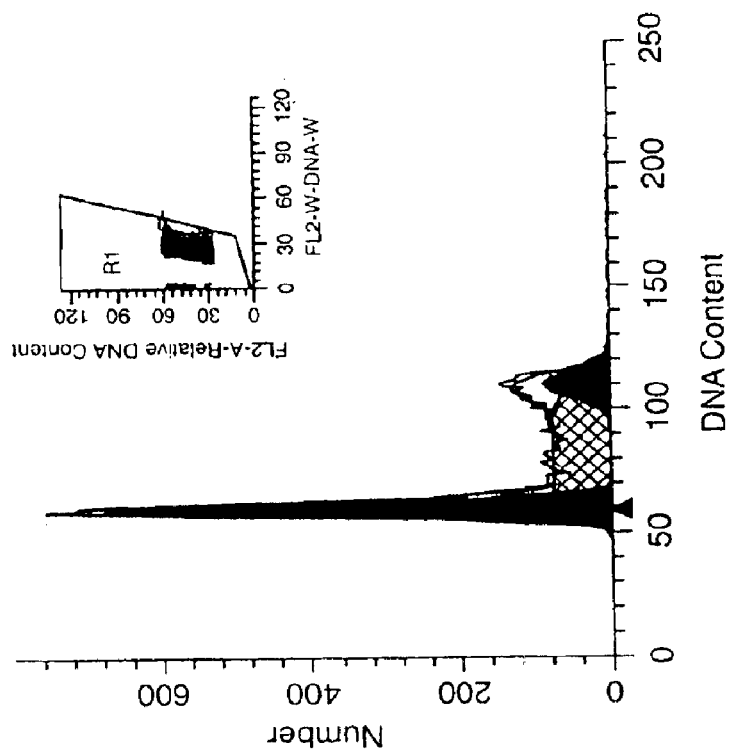
FIGS. 2A and 2B. Cell cycle stage distribution of logaritmically replicating PC12 (A) and ECV304 (B) cell culture. Cells at approximately 70% confluence were harvested and prepared for cell cycle analysis. DNA content of cells was determined by flow cytometry. Each data points represent the mean fluorescence for 10,000 cells. Statistical analysis was carried out using ModFitLT V2.0 software.
Figure 2A:
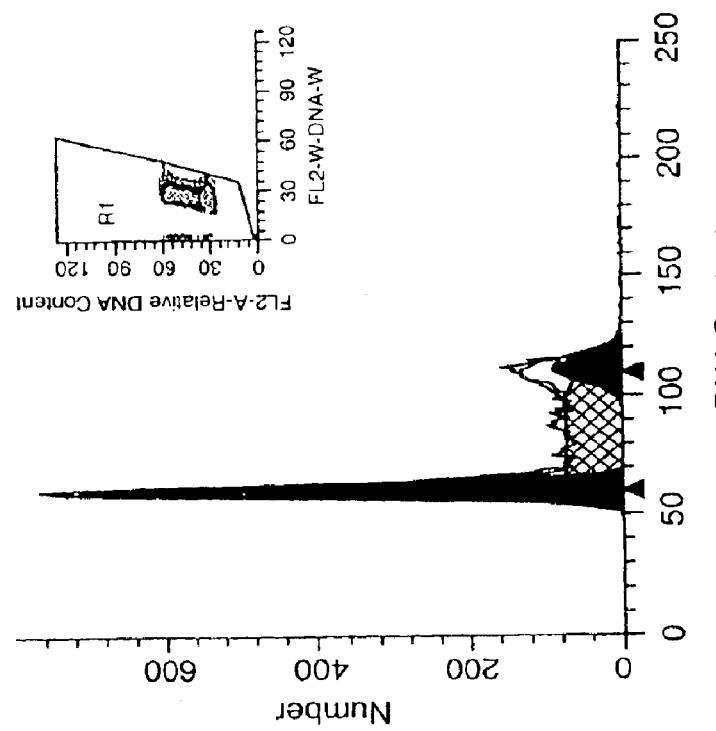
Figure 3B:
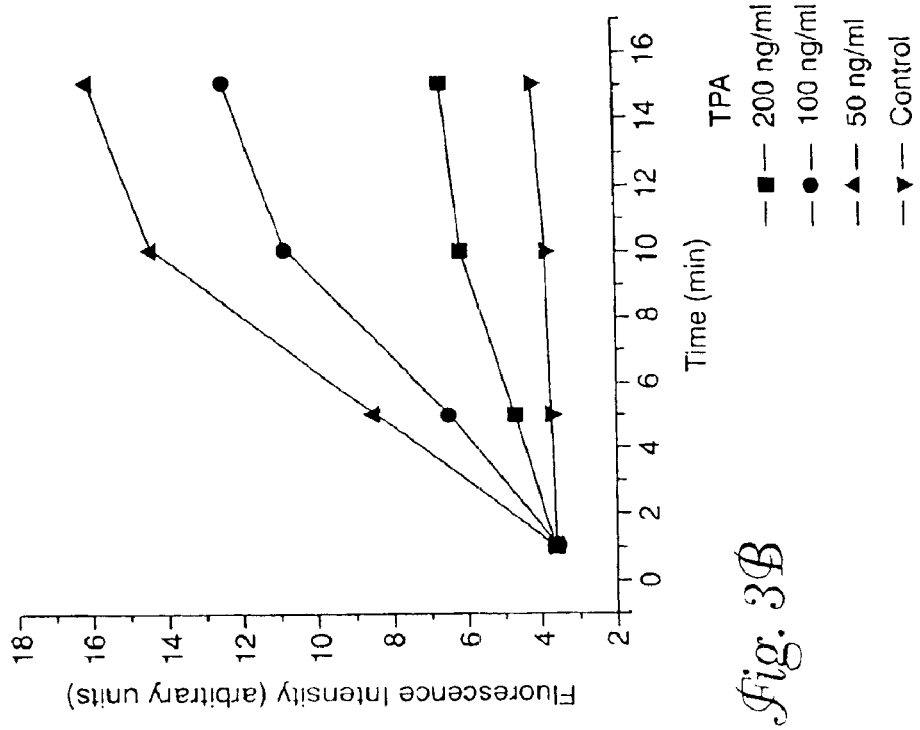
FIGS. 3A and 3B. Change in DCF fluorescence intensity as function of time, after addition of $H_2O_2$ or TPA to PC12 cells. Cells ($10^6$) were loaded with $H_2$DCF-DA (2.5 micromolar ($\mu$M)) for 12 minutes (min) and increasing concentrations of $H_2O_2$ (0, 12.5, 25 50 and 100 $\mu$M) or TPA (0, 50, 100, and 200 nanograms per milliliter (ng/ml)) was added. Fluorescence intensities were determined at 0, 5, 10 and 15 minutes after addition of $H_2O_2$ or TPA addition. Each data point represents the mean fluorescence for 10,000 cells.
Figure 3A:
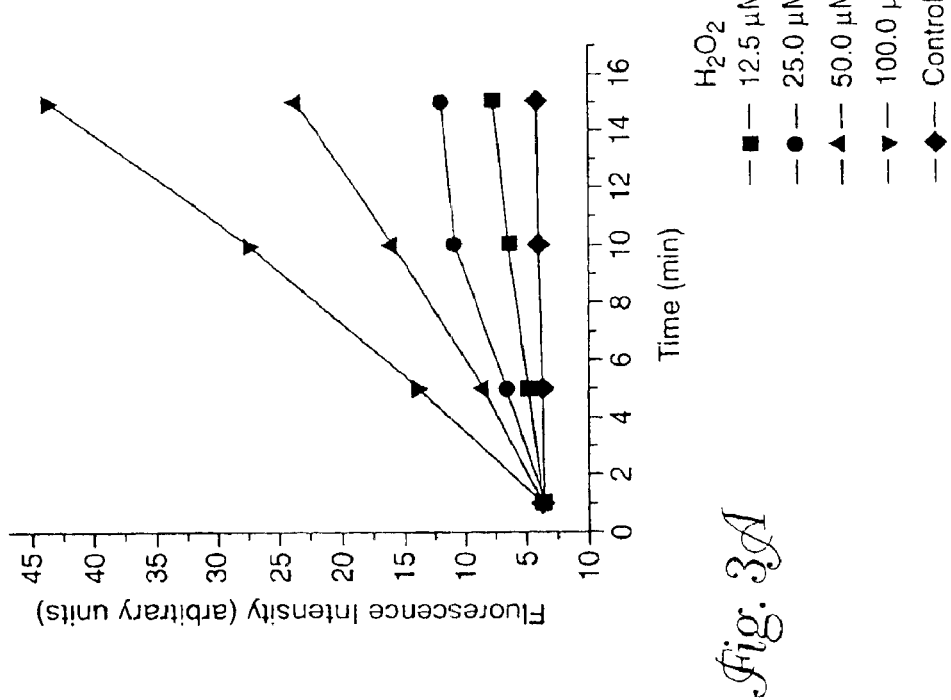
Figure 4:
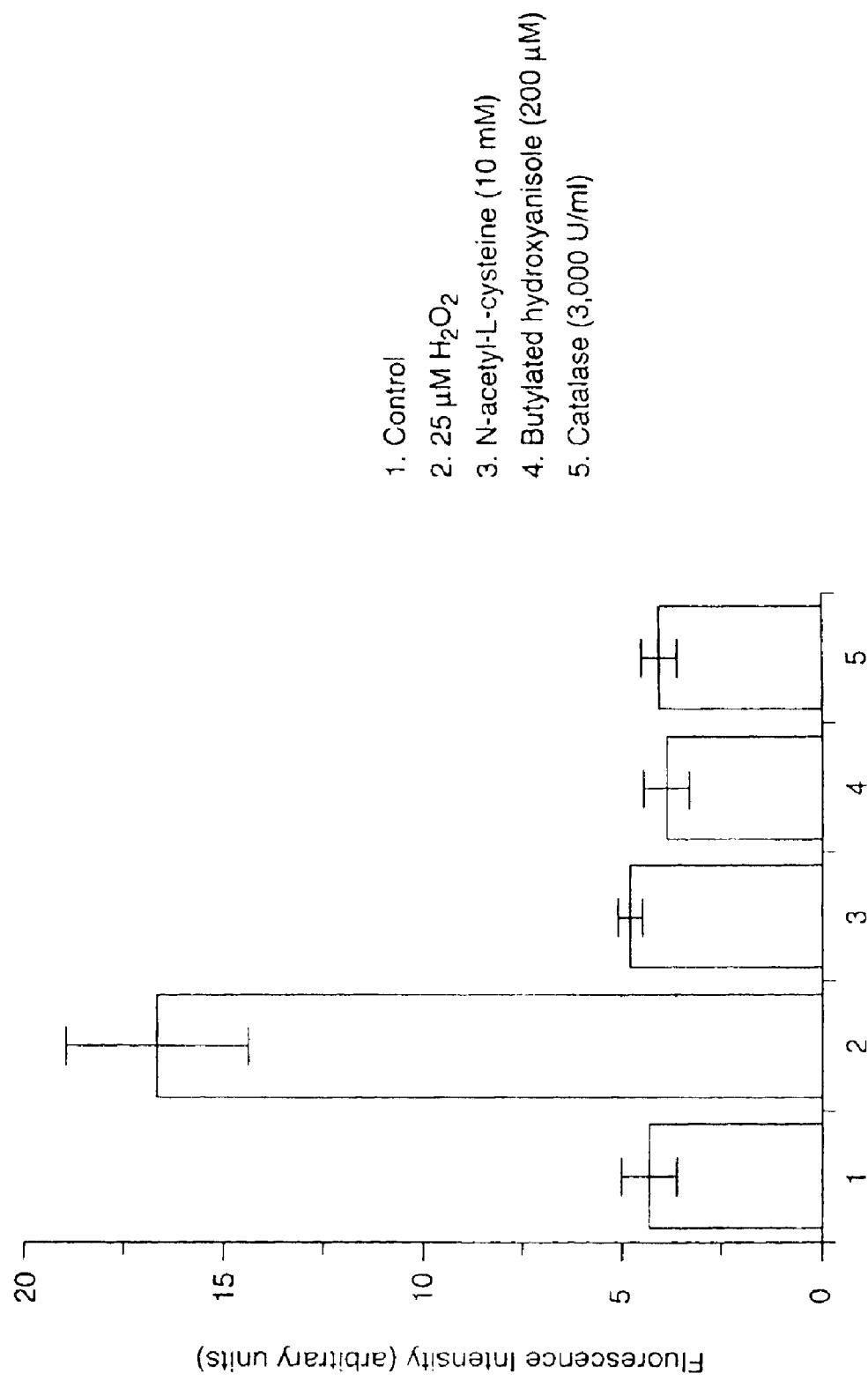
FIG. 4. Effect of N-acetyl-L-cysteine, butylated hydroxyanisole, and catalase on $H_2O_2$-induced $H_2$DCF oxidation. Treated and non-treated cells, loaded with $H_2$DCF-DA (2.5 $\mu$M) were exposed to 25 $\mu$M $H_2O_2$ and changes in fluorescence intensities were determined at 0 and 15 min by flow cytometry. Each data points represent the mean fluorescence for 10,000 cells.
Figure 5:
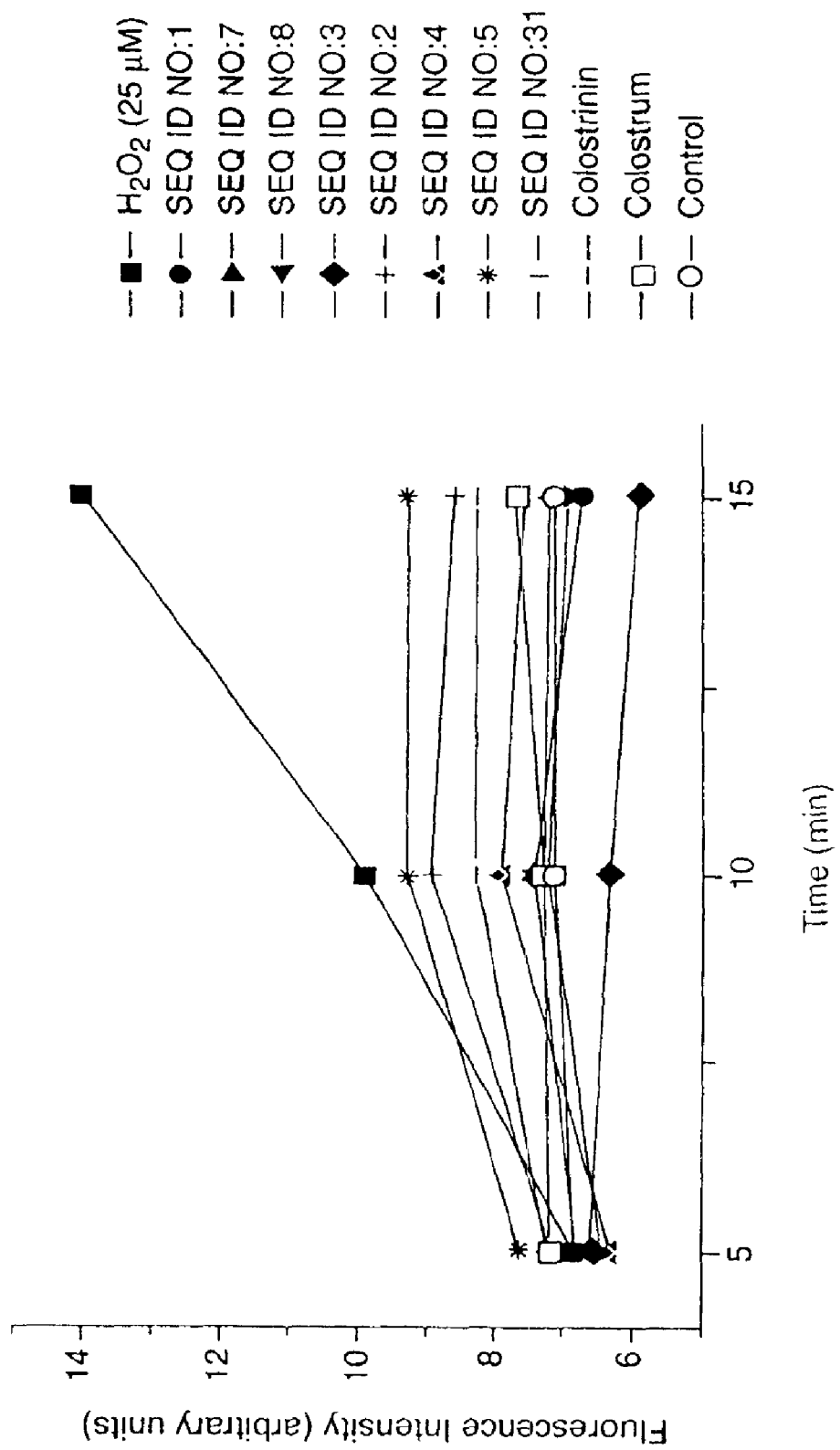
FIG. 5. Effect of colostrum, colostrinin, and its constituent peptides. Cells were $H_2$DCF-DA loaded and treated with compounds as described in the Examples Section. Changes in fluorescence intensity of treated and mock-treated cell cultures were determined as a function time (0, 5, 10, 15 minutes) after addition of 25 $\mu$M $H_2O_2$. The concentrations of colostrum colostrinin, and its constituent peptides were 10 micrograms per milliliter ($\mu$g/ml). Each data points represent the mean fluorescence for 10,000 cells.
Figure 6:
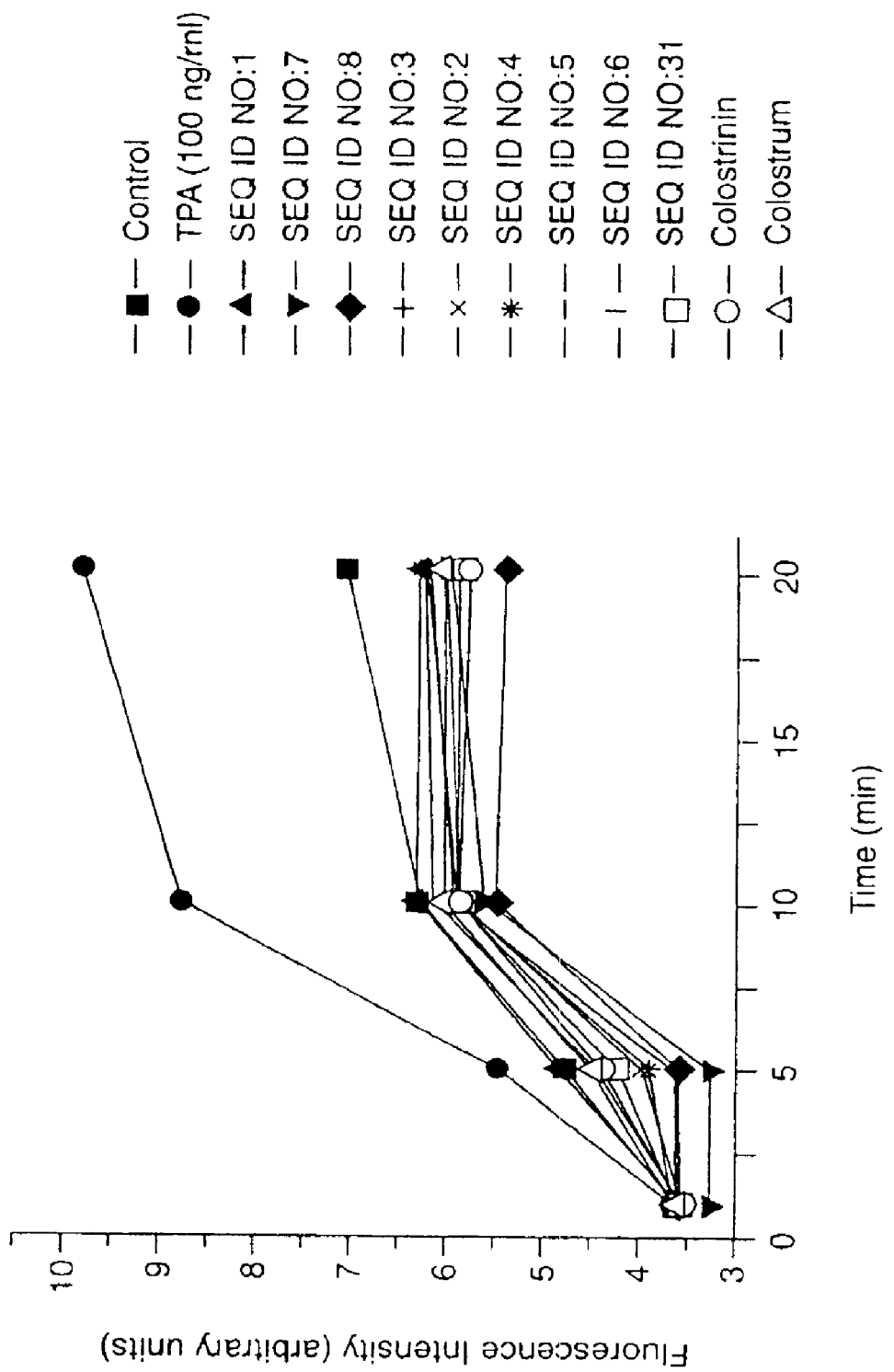
FIG. 6. Reduction in TPA-induced reactive oxidizing species (ROS) levels in the presence of colostrum, colostrinin, and its constituent peptides as a function of time. Cells were $H_2$DCF-DA loaded and treated with compounds as described in the Examples Section. Changes in fluorescence intensity of treated and mock-treated cell cultures were determined as a function time (0, 5, 10, 15 minutes) after addition of 100 nanograms (ng) TPA. The concentrations of colostrum, colostrinin, and its constituent peptides were 10 $\mu$g/ml. Each data points represent the mean fluorescence for 10,000 cells.
Figure 7:
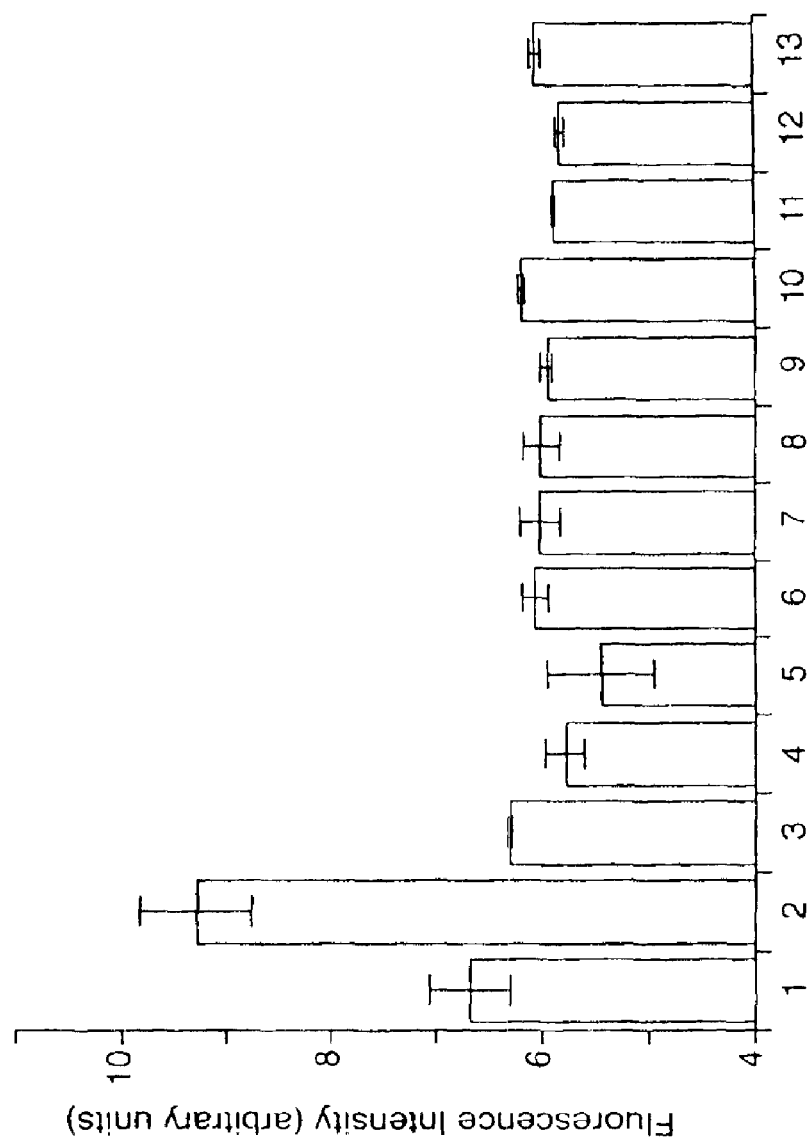
FIG. 7. Reduction in ROS levels by colostrum, colostrin, and its constituent peptides from three independent experiments. $H_2$DCF-DA-loaded cells were treated with compounds as described in the Examples Section. Changes in fluorescence intensity of treated and mock-treated cell cultures were determined as a function time (0, 5, 10, 15 minutes) after addition of 100 ng TPA. The concentrations of colostrum, colostrinin, and its constituent peptides were 10 $\mu$g/ml. Each data points represent the mean fluorescence for 10,000 cells.

Cell viability assay: Cell viability was determined by flow cytometry after staining cells ($10^6$) with 1 µM propidium iodine. Cell suspensions with a viability of more than 95%, were used. Cell cycle stage distribution was determined by DNA content measurement. A typical histogram is shown in FIG. 2.

Materials: N-acetyl-L-cysteine, catalase, butylated hydroxyanisole and $H_2O_2$ were purchased from Sigma Chemicals Co. (St. Louis, Mo.). DCF, 2'-7'-dichlorofluorescin diacetate, and propidium iodine were purchased from Molecular Probes (Eugene, Oreg.). Catalase (from beef liver, 65,000 U/mg crystalline suspension in water) was obtained from Boehringer-Mannheim (Indianapolis, Ind.). Stock solutions were prepared according to manufacturers' recommendations. RPMI-1640 and M199 and other medium supplements were purchased from Gibco-BRL, and fetal bovine serum was obtained from Hyclone, Inc.

Results

Data summarized in attached Figures show that constituent peptides of colostrinin, colostrinin itself, and colostrum have significant oxidative stress regulating activity. These compounds did not interfere with cellular uptake of redox-sensitive 2',7'-dihydro-dichlorofluorescein-diacetate. Also colostrum or colostrinin and its constituent peptides do not directly oxidize or reduce $H_2DCF$ and DCF, respectively (data not shown). The oxidative stress regulating activity of SEQ ID NO:1, SEQ ID NO:7, SEQ ID NO:8, SEQ ID NO:3, SEQ ID NO:2, SEQ ID NO:4, and SEQ ID NO:5, SEQ ID NO:31, colostrinin, and colostrum was similar in both PC12 (medullary pheochromocytoma) and ECV304 (immortalized human endothelial cells developed from the umbilical vein) cells indicating that their effect is not cell type specific (in this report data generated using PC12 cells are shown).

Although the invention has been disclosed with reference to its preferred embodiments, from reading this description those of skill in the art may appreciate changes and modification that may be made which do not depart from the scope and spirit of the invention as described above and claimed hereafter.

All references, patents, and patent applications cited herein are incorporated herein by reference in their entirety as if individually incorporated.

Sequence Listing Free Text

The following are all synthetic peptide sequences.

| | |
|---|---|
| SEQ ID NO:1 | MQPPPLP |
| SEQ ID NO:2 | LQTPQPLLQVMMEPQGD |
| SEQ ID NO:3 | DQPPDVEKPDLQPFQVQS |
| SEQ ID NO:4 | LFFFLPVVNVLP |
| SEQ ID NO:5 | DLEMPVLPVEPFPFV |
| SEQ ID NO:6 | MPQNFYKLPQM |
| SEQ ID NO:7 | VLEMKFPPPPQETVT |
| SEQ ID NO:8 | LKPFPKLKVEVFPFP |
| SEQ ID NO:9 | VVMFV |
| SEQ ID NO:10 | SEQP |
| SEQ ID NO:11 | DKE |
| SEQ ID NO:12 | FPPPK |
| SEQ ID NO:13 | DSQPPV |
| SEQ ID NO:14 | DPPPPQS |
| SEQ ID NO:15 | SEEMP |
| SEQ ID NO:16 | KYKLQPE |

-continued

| SEQ ID NO:17 | VLPPNVG |
| SEQ ID NO:18 | VYPFTGPIPN |
| SEQ ID NO:19 | SLPQNILPL |
| SEQ ID NO:20 | TQTPVVVPPF |
| SEQ ID NO:21 | LQPEIMGVPKVKETMVPK |
| SEQ ID NO:22 | HKEMPFPKYPVEPFTESQ |
| SEQ ID NO:23 | SLTLTDVEKLHLPLPLVQ |
| SEQ ID NO:24 | SWMHQPP |
| SEQ ID NO:25 | QPLPPTVMFP |
| SEQ ID NO:26 | PQSVLS |
| SEQ ID NO:27 | LSQPKVLPVPQKAVPQRDMPIQ |
| SEQ ID NO:28 | AELLYQE |
| SEQ ID NO:29 | RGPFPILV |
| SEQ ID NO:30 | ATFNRYQDDHGEEILKSL |
| SEQ ID NO:31 | VESYVPLFP |
| SEQ ID NO:32 | FLLYQEPVLGPVR |
| SEQ ID NO:33 | LNF |
| SEQ ID NO:34 | MHQPPQPLPPTVMFP |

We claim:

1. A topical formulation comprising an oxidative stress regulator selected from the group consisting of a constituent peptide of colostrinin, an active analog of a constituent peptide of colostrinin, and combinations thereof; wherein the constituent peptide of colostrinin is selected from the group consisting of MQPPPLP (SEQ ID NO:1), LQTPQ-PLLQVMMEPQGD (SEQ ID NO:2), DQPPDVEKP-DLQPFQVQS (SEQ ID NO:3), LFFFLPVVNVLP (SEQ ID NO:4), DLEMPVLPVEPFPFV (SEQ ID NO:5), MPQN-FYKLPQM (SEQ ID NO:6), VLEMKPPPPPQETVT (SEQ ID NO:7), and LKPFPKLKVEVFPFP (SEQ ID NO:8); and wherein the active analog of a constituent peptide of colostrinin comprises a peptide having an amino acid sequence with at least about 15 percent proline and having at least about 70 percent sequence identity to a constituent peptide of colostrinin selected from the group consisting of SEQ ID NO:1–8.

2. The topical formulation of claim 1 which is in the form of a sunscreen.

3. The topical formulation of claim 1 wherein the oxidative stress regulator is selected from the group consisting of MQPPPLP (SEQ ID NO:1), LQTPQPLLQVMMEPQGD (SEQ ID NO:2), DQPPDVEKPDLQPFQVQS (SEQ ID NO:3), LFFFLPVVNVLP (SEQ ID NO:4), DLEMPV-LPVEPFPFV (SEQ ID NO:5), MPQNFYKLPQM (SEQ ID NO:6), VLEMKPPPPQETVT (SEQ ID NO:7), LKPFP-KLKVEVFPFP (SEQ ID NO:8), and combinations thereof.

4. The topical formulation of claim 1 which is in the form of a cosmetic formulation.

5. A topical formulation comprising an oxidative stress regulator selected from the group consisting of a constituent peptide of colostrinin, an active analog of a constituent peptide of colostrinin, and combinations thereof; wherein a the constituent peptide of colostrinin is selected from the group consisting of MQPPPLP (SEQ ID NO:1), LQTPQ-PLLQVMMEPQGD (SEQ ID NO:2), DQPPDVEKP-DLQPFQVQS (SEQ ID NO:3), LFFFLPVVNVLP (SEQ ID NO:4), DLEMPVLPVEPFPFV (SEQ ID NO:5), MPQN-FYKLPQM (SEQ ID NO:6), VLEMKFPPPPQETVT (SEQ ID NO:7), and LKPFPKLKVEVFPFP (SEQ ID NO:8); wherein the active analog of a constituent peptide of colostrinin comprises a peptide having an amino acid sequence with at least about 15 percent proline and having at least about 70 percent sequence identity to a constituent peptide of colostrinin selected from the group consisting of SEQ ID NO:1–8 and further wherein the active analog of a constituent peptide of colostrinin does not interfere with cellular uptake of redox-sensitive 2',7'-dihydro-dichlorofluorescein-diacetate.

6. The topical formulation of claim 5 which is in the form of a cosmetic formulation.

7. The topical formulation of claim 5 which is in the form of a skincare cream.

8. The topical formulation of claim 5 which is in the form of a decorative make-up product.

9. The topical formulation of claim 5 which is in the form of a sunscreen.

10. The topical formulation of claim 9 further comprising a UVA filter, a UVB filter, or combinations thereof.

11. The topical formulation of claim 5 comprising a lipid phase.

12. The topical formulation of claim 5 comprising an aqueous phase.

13. The topical formulation of claim 5 further comprising preservatives, bactericides, perfumes, antifoams, dyes, pigments, surfactants, thickeners, suspending agents, fillers, moisturizers, humectants, fats, oils, waxes, alcohols, polyols, polymers, foam stabilizers, electrolytes, organic solvents, or combinations thereof.

14. A topical formulation comprising colostrinin and a UVA filter, a UVB filter, or a combination of a UVA filter and a UVB filter.

15. A topical formulation comprising a peptide selected from the group consisting of MQPPPLP (SEQ ID NO:1), LQTPQPLLQVMMEPQGD (SEQ ID NO:2), DQPPD-VEKPDLQPFQVQS (SEQ ID NO:3), LFFFLPVVNVLP (SEQ ID NO:4), DLEMPVLPVEPFPFV (SEQ ID NO:5), MPQNFYKLPQM (SEQ ID NO:6), VLEMKFPPP-PQETVT (SEQ ID NO:7), LKPFPKLKVEVFPFP (SEQ ID NO:8), and combinations thereof.

16. The topical formulation of claim 15 which is in the form of a cosmetic formulation.

17. The topical formulation of claim 15 which is in the form of a skincare cream.

18. The topical formulation of claim 15 which is in the form of a sunscreen.

19. The topical formulation of claim 15 which is in the form of a decorative make-up product.

20. A topical formulation comprising an oxidative stress regulator selected from the group consisting of an active analog of a constituent peptide of colostrinin, and combinations thereof; wherein the active analog of a constituent peptide of colostrinin comprises a peptide having an amino acid sequence with at least about 15 percent proline and having at least about 70 percent sequence identity to a constituent peptide of colostrinin selected from the group consisting of SEQ ID NO:1 through SEQ ID NO:8, and SEQ ID NO:31; and further wherein the active analog of a constituent peptide of colostrinin does not interfere with cellular uptake of redox-sensitive 2',7'-dihydro-dichlorofluorescein-diacetate.

21. The topical formulation of claim 20 which is in the form of a cosmetic formulation.

22. The topical formulation of claim 20 which is in the form of a skincare cream.

23. The topical formulation of claim 20 which is in the form of a sunscreen.

24. The topical formulation of claim 20 which is in the form of a decorative make-up product.

* * * * *

UNITED STATES PATENT AND TRADEMARK OFFICE
CERTIFICATE OF CORRECTION

PATENT NO. : 6,939,847 B2
DATED : September 6, 2005
INVENTOR(S) : Stanton et al.

It is certified that error appears in the above-identified patent and that said Letters Patent is hereby corrected as shown below:

Column 14,
Line 55, delete "VVMFV" and insert -- VVMEV --;

Column 16,
Line 6, delete "AELLYQE" and insert -- AFLLYQE --;

Column 27,
Line 47, delete "VLEMKPPPPPQETVT" and insert -- VLEMKPPPPQETVT --.

Signed and Sealed this

Seventh Day of March, 2006

JON W. DUDAS
*Director of the United States Patent and Trademark Office*